(12) United States Patent
Keller et al.

(10) Patent No.: US 6,702,840 B2
(45) Date of Patent: *Mar. 9, 2004

(54) HEAT EXCHANGE CATHETER WITH DISCRETE HEAT EXCHANGE ELEMENTS

(75) Inventors: Wade E. Keller, San Jose, CA (US); Timothy R. Machold, Moss Beach, CA (US); Mark A. Saab, Lowell, MA (US)

(73) Assignee: Radiant Medical, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/907,799

(22) Filed: Jul. 18, 2001

(65) Prior Publication Data

US 2001/0044644 A1 Nov. 22, 2001

Related U.S. Application Data

(63) Continuation of application No. 09/378,578, filed on Aug. 20, 1999, now Pat. No. 6,264,679.

(51) Int. Cl.[7] .................................................. A61F 7/00
(52) U.S. Cl. ........................ 607/105; 607/104; 607/106
(58) Field of Search .......................... 607/96, 105, 113; 6060/21–23, 27–28

(56) References Cited

U.S. PATENT DOCUMENTS 5,624,392 A * 4/1997 Saab ......................... 604/113
5,837,003 A * 11/1998 Ginsburg ..................... 606/27
5,899,899 A * 5/1999 Arless et al. .................. 606/20
6,126,684 A * 10/2000 Gobin et al. ................. 604/113
6,338,727 B1 * 1/2002 Noda et al. .................. 604/113
6,450,990 B1 * 9/2002 Walker et al. ............... 604/113

* cited by examiner

*Primary Examiner*—Roy D. Gibson
(74) *Attorney, Agent, or Firm*—Robert D. Buyan; Stout, Uxa, Buyan & Mullins, LLP.

(57) ABSTRACT

A catheter for exchanging heat with a body fluid is disclosed. The catheter includes a main shaft and a heat exchange region having a plurality of heat exchange elements each having a length and opposed ends. Each of the elements is attached on at least one of its ends to the shaft and disposed so that when inserted in a fluid body cavity having body fluid therein, the body fluid may circumferentially surround each heat exchange element along a portion of the length of the heat exchange element. The catheter includes a fluid circulation path therein, which desirably includes the hollow lumen within each of heat exchange elements. The heat exchange elements may be connected at two points along the shaft using manifolds that are in fluid communication with fluid flow paths within the shaft. Alternatively, the heat exchange elements may be connected at only one point and be permitted to float in a proximal or distal direction with respect to the catheter. The heat exchange region may be formed on a distal portion of the catheter, or may be formed along the entire length thereof. In the former configuration, an insulating member, such as a balloon, may be provided along the shaft proximal to the heat exchange region. Ribs may be provided on each heat exchange element to disrupt flow therearound and increase heat exchange. Each of the heat exchange elements may be non-circular in cross-section, and may extend in an undulating path with respect to the catheter shaft.

10 Claims, 15 Drawing Sheets

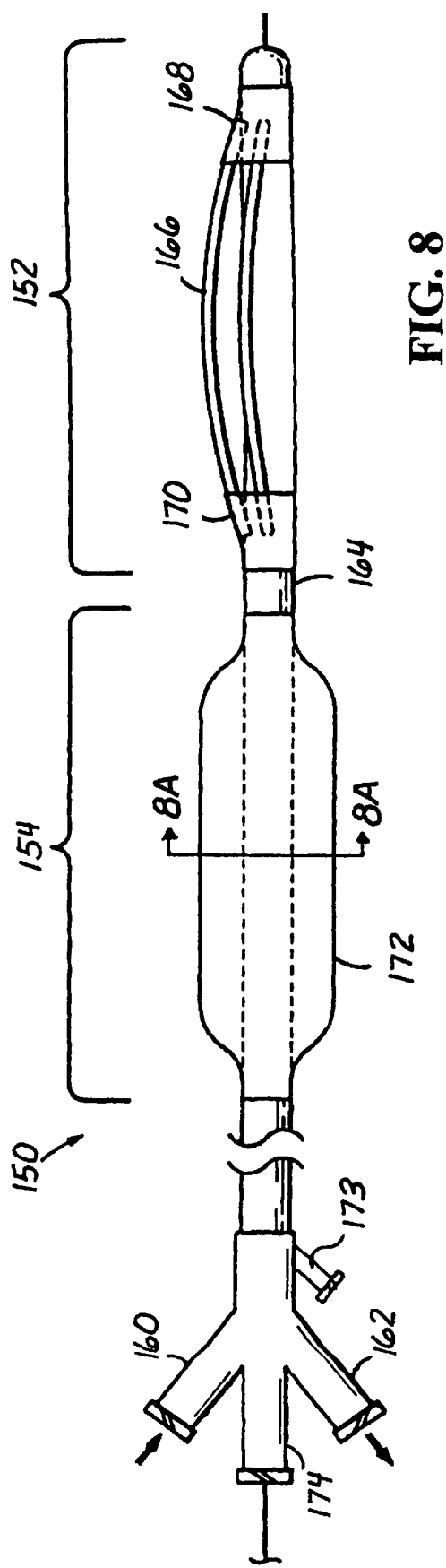
FIG. 8
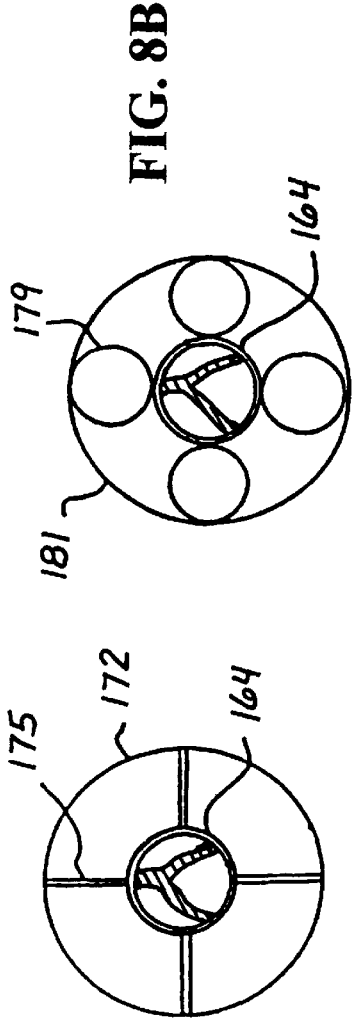
FIG. 8B
FIG. 8A

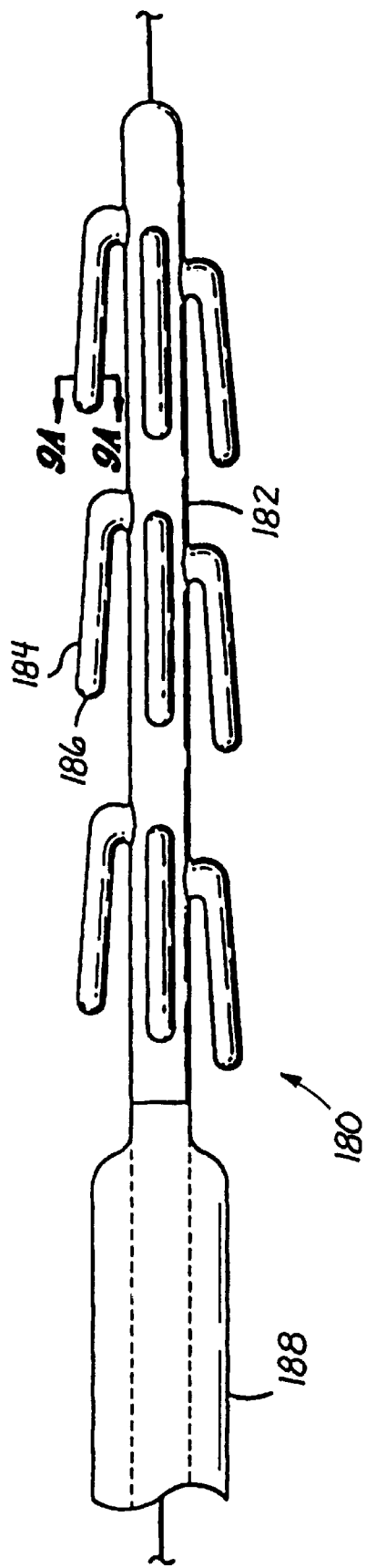
FIG. 9
FIG. 9A

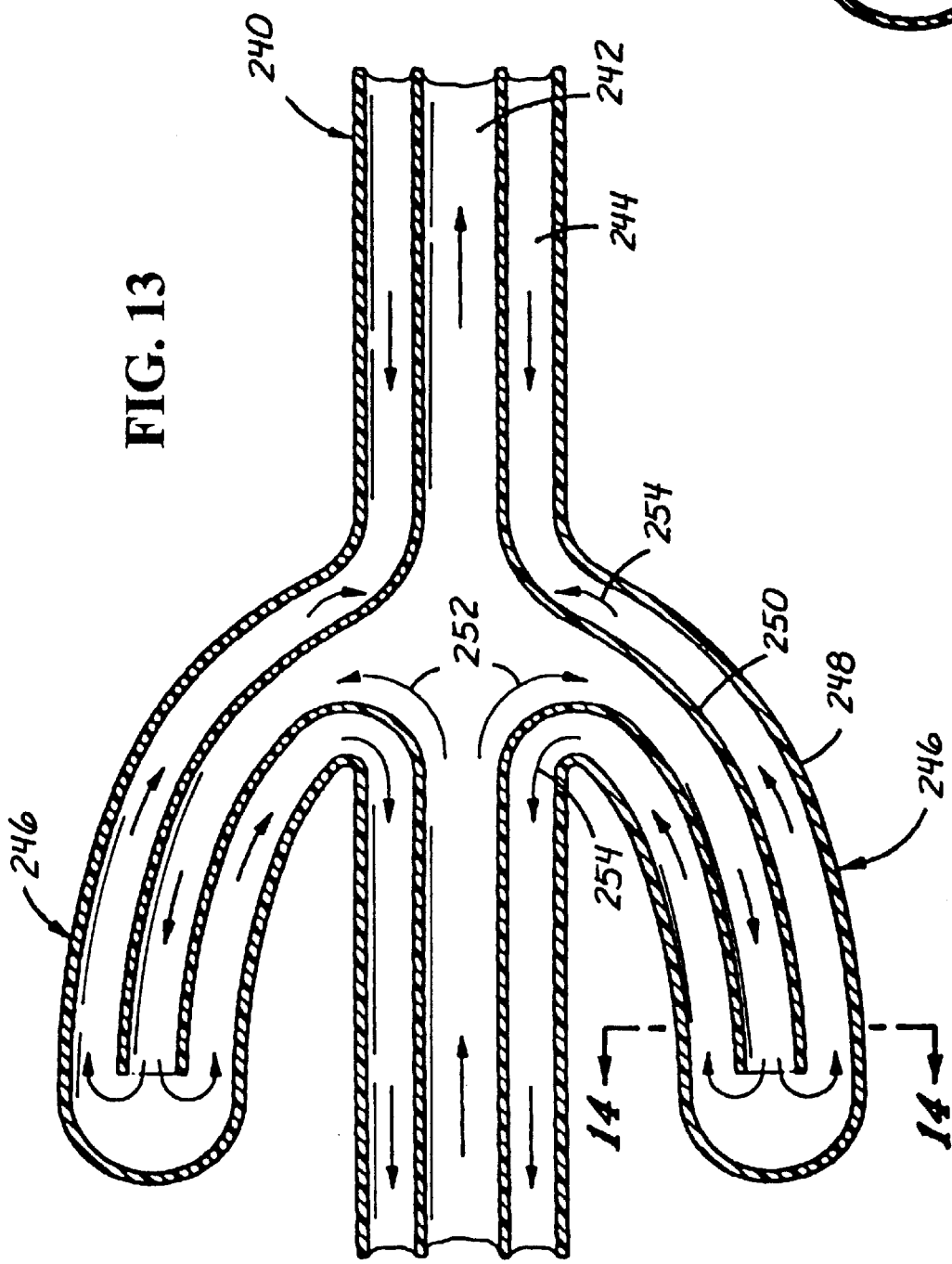

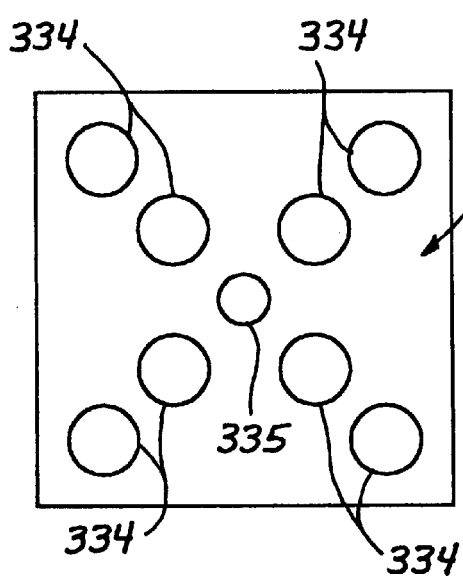
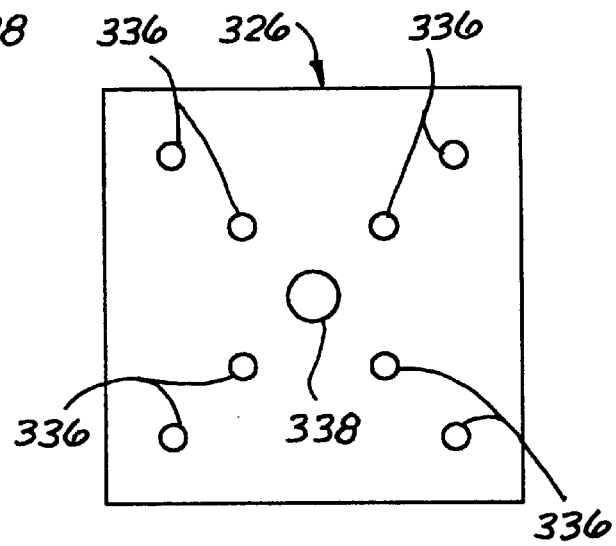
FIG. 19  FIG. 20
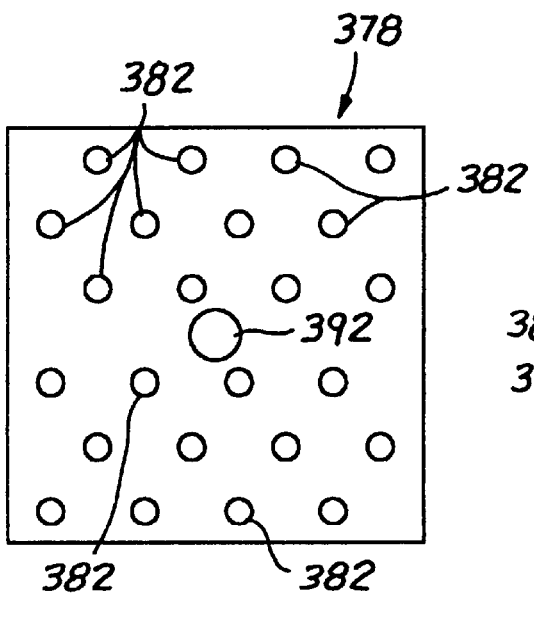
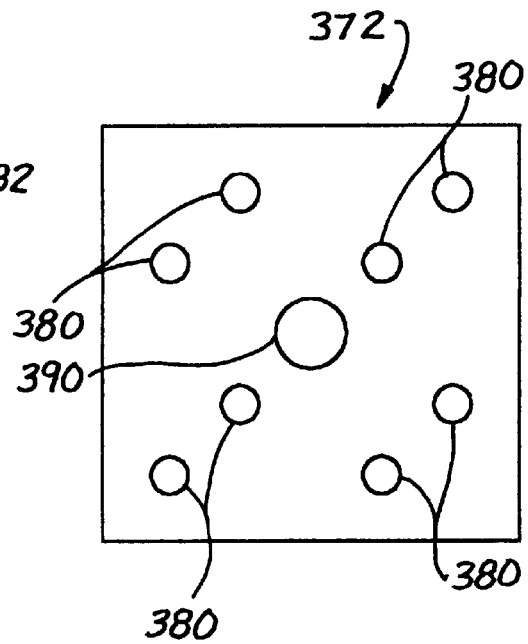
FIG. 25  FIG. 26

US 6,702,840 B2

HEAT EXCHANGE CATHETER WITH DISCRETE HEAT EXCHANGE ELEMENTS

This patent application is a continuation of application Ser. No. 09/378,578 filed on Aug. 20, 1999 now U.S. Pat. No. 6,264,679.

FIELD OF THE INVENTION

This invention relates generally to medical devices and methods and more particularly to devices and methods for selectively controlling the temperature of a patient's body, or portion of the patients body, by adding or removing heat from the patient's body fluid through the use of a heat exchange catheter that incorporates a plurality of discrete heat exchange elements in the nature of filaments or tubular members.

BACKGROUND OF THE INVENTION

Under ordinary circumstances, thermoregulatory mechanisms exist in the healthy human body to maintain the body at a constant temperature of about 37° C. (98.6° F.), a condition sometimes referred to as normothermia. To maintain normothermia, the thermoregulatory mechanisms act so that heat lost to the environment is replaced by the same amount of heat generated by metabolic activity in the body. For various reasons, a person may develop a body temperature that is below normal, a condition known as hypothermia.

Accidental hypothermia may result when heat loss to the environment exceeds the body's ability to produce heat internally or when a person's thermoregulatory ability has been lessened due to injury, illness or anesthesia. Accidental hypothermia is generally a dangerous condition that can have serious medical consequences. For example, hypothermia may interfere with the ability of the heart to pump blood or the ability of the blood to clot normally. Hypothermia may also interfere with various temperature sensitive enzymatic reactions in the body with resultant metabolic and biochemical consequences, and has sometimes been associated with impaired immune response and increased incidence of infection.

Simple methods for treating hypothermia have been known since very early times. Such methods include wrapping the patient in blankets, administering warm fluids by mouth, and immersing the patient in a warm water bath. If the hypothermia is not too severe, these methods may be effective. However, wrapping a patient in a blanket depends on the ability of the patient's own body to generate heat to re-warm the body. Administering warm fluids by mouth relies on the patient's ability to swallow, and is limited in the temperature of the liquid consumed, and the amount of fluid that may be administered in a limited period of time. Immersing a patient in warm water is often impractical, particularly if the patient is simultaneously undergoing surgery or some other medical procedure.

More recently, hypothermia may be treated by the application of a warming blanket that applies heat to the skin of the patient. Applying heat to the patient's skin, however, may be ineffective in providing heat to the core of the patient's body. Heat applied to the skin has to transmit through the skin by conduction or radiation which may be slow and inefficient, especially if the patient has a significant layer of fat between the warming blanket and the body's core.

Paradoxically, the application of warmth to a hypothermic patient's skin, whether by immersion in hot water or application of a warm blanket, may actually exacerbate the problem and may even induce shock. The body has certain thermoregulatory responses to cold that work to conserve heat in the body's core, specifically vasoconstriction and arterio-venous shunting (AV shunts). Vasoconstriction occurs when the capillaries and other blood vessels in the skin and extremities constrict so that most of the blood pumped by the heart circulates through the core rather than through the skin and extremities. Similarly, in AV shunting, naturally occurring blood shunts exist between some arteries providing blood to capillary beds in the skin and extremities and veins returning blood from those capillary beds. When the body is cooled, those shunts may be opened, allowing blood to by-pass those capillary beds altogether. Thus when the body is cooled, the tissues in the extremities, and particularly at the surface, have little blood flowing to them and may become quite cold relative to the body's core temperature.

When heat is applied to the skin of a hypothermic patient, the temperature sensors in the skin may cause the vasoconstriction to reverse and the AV shunts to close. When this happens, blood from the core floods into the very cold tissue on the body surface and extremities, and as a result the blood loses heat to those tissues, often far more than the amount of heat being added by the surface warming. As a result, the victim's core temperature may plummet and the patient may even go into shock.

Partly in response to the inadequacies of surface application of heat, methods have been developed for adding heat to a patient's body by internal means. A patient being administered breathing gases, for example a patient under anesthesia, may have the breathing gases warmed. This method may be effective but is limited in the amount of heat that can be administered without injuring the lungs. Similarly, a patient receiving IV fluids may have the fluids warmed, or a bolus of warm fluid may be administered intravenously. This may be effective in the case of mild hypothermia, but the temperature of the IV fluid is limited by the temperature that will be destructive to the blood, generally thought to be about 41° C.–49° C., and the amount of fluid that is acceptable to administer to a particular patient.

A more invasive method may be used to add heat to a patient's blood, particularly in the case of heart surgery. Blood is removed from a patient, circulated through a cardiopulmonary by-pass (CPB) system, and reintroduced into the patient's body. The blood may be heated or cooled before being reintroduced into the patient. This CPB method is both fast and effective in adding or removing heat from a patient's blood, but has the disadvantage of involving a very invasive medical procedure which requires the use of complex equipment, a team of highly skilled operators, and is generally only available in a surgical setting. It also involves mechanical pumping of blood which is generally very destructive of the blood tissue resulting in the cytotoxic and thrombolytic problems associated with removal of blood from the body, mechanical pumping of the blood, and channeling the blood through various machines and lines.

Means for adding heat to the core of the body that do not involve pumping the blood with an external, mechanical pump have been suggested. For example, a method of treating hypothermia or hyperthermia by means of a heat exchange catheter placed in the bloodstream of a patient was described in U.S. Pat. No. 5,486,208 to Ginsburg, the complete disclosure of which is incorporated herein by reference. That patent discloses a method of treating or inducing hypothermia by inserting a heat exchange catheter having a heat exchange area including a balloon with heat exchange fins into the bloodstream of a patient, and circulating heat exchange fluid through the balloon while the balloon is in contact with the blood to add or remove heat from the bloodstream. (As used herein, a balloon is a structure that is readily inflated under pressure and collapsed under vacuum.) Under certain conditions heat is generated within the body or heat is added from the environment in excess of the body's ability to dissipate heat and a persons develops a condition of abnormally high body temperature, a condition known as hyperthermia. Examples of this condition may result from exposure to a hot and humid environment or surroundings, overexertion, or exposure to the sun while the body's thermoregulatory mechanisms are disabled by drugs or disease. Additionally, often as a result of injury or disease, a person may establish a set point temperature that is above the normal body temperature of about 37° C. The set point temperature is the temperature that the body's thermoregulatory mechanisms act to maintain. Under ordinary circumstances, this is about 37° C. but in other cases, such as fever, the body may establish a different set point temperature and act to maintain that temperature.

Like hypothermia, hyperthermia is a serious condition that may sometimes be fatal. In particular, hyperthermia has been found to be neurodestructive, both in itself or in conjunction with other health problems such as stroke, where a body temperature in excess of normal in conjunction with a stroke or traumatic brain injury has been shown to results in dramatically worse outcome.

As with hypothermia, counter-parts to simple methods for treating the condition exist, such as cold water baths and cooling blankets, and more effective but complex and invasive means such as cooled breathing gases and blood cooled during CPB also exist. These, however, are subject to the limitations and complications as described above in connection with hypothermia. In addition, the thermoregulatory responses such as vasoconstriction, AV shunting and shivering, may act directly to combat the attempt to cool the patient and thereby defeat the effort to treat the hyperthermia. This is especially true in the case of fever, where the body may establish a set point temperature higher than normothermia and actively resist efforts to reduce the body's feverish temperature to normothermia.

Although both hypothermia and hyperthermia may be harmful and require treatment in some case, in other cases hyperthermia, and especially hypothermia, may be therapeutic or otherwise advantageous, and therefore may be intentionally induced. For example, periods of cardiac arrest in myocardial infarction and heart surgery can produce brain damage or other nerve damage. Hypothermia is recognized in the medical community as an accepted neuroprotectant and therefore a patient is often kept in a state of induced hypothermia during cardiovascular surgery. Likewise, hypothermia is sometimes induced as a neuroprotectant during neurosurgery.

It is sometimes desirable to induce whole-body or regional hypothermia for the purpose of treating, or minimizing the adverse effects of, certain neurological diseases or disorders such as head trauma, spinal trauma and hemorrhagic or ischemic stroke. Additionally, it is sometimes desirable to induce whole-body or regional hypothermia for the purpose of facilitating or minimizing adverse effects of certain surgical or interventional procedures such as open heart surgery, aneurysm repair surgeries, endovascular aneurysm repair procedures, spinal surgeries, or other surgeries where blood flow to the brain, spinal cord or vital organs may be interrupted or compromised. Hypothermia has also been found to be advantageous to protect cardiac muscle tissue after a myocardial infarct (MI).

Neural tissue such as the brain or spinal cord, is particularly subject to damage by vascular disease processes including, but not limited to ischemic or hemorrhagic stroke, blood deprivation for any reason including cardiac arrest, intracerebral or intracranial hemorrhage or blockage, and head trauma. In each of these instances, damage to brain tissue may occur because of brain ischemia, increased intracranial pressure, edema or other processes, often resulting in a loss of cerebral function and permanent neurological deficits. Although the exact mechanism for neuroprotection is not fully understood, lowering the brain temperature is believed to effect neuroprotection through several mechanisms including, the blunting of any elevation in the concentration of neurotransmitters (e.g., glutamate) occurring after ischemic insult, reduction of cerebral metabolic rate, moderation of intracellular calcium transport/metabolism, prevention of ischemia-induced inhibitions of intracellular protein synthesis and/or reduction of free radical formation as well as other enzymatic cascades and even genetic responses. Thus intentionally induced hypothermia may prevent some of the damage to brain or other neurological tissue during surgery or as a result of stroke, intracerebral hemorrhage and trauma.

Intentionally inducing hypothermia has generally been attempted by either surface cooling or by-pass pumping. Surface cooling has generally proved to be unacceptably slow, since the body heat to be removed must be transmitted from the core to the surface, and has sometimes been altogether unsuccessful since the body's thermoregulatory mechanisms act to prevent surface cooling from reducing the core temperature of the body. For example, the vasoconstriction and AV shunting may prevent heat generated in the core from being transmitted to the surface by the blood. Thus the surface cooling may only succeed in cooling the skin and surface tissue, and not succeed in reducing the core temperature of the patient to induce a hypothermic state.

Another thermoregulatory mechanism that may thwart attempts to reduce core temperature by surface cooling is shivering. There are numerous temperature sensors on the body's surface, and these may trigger the body to begin shivering. Shivering results in the generation of a significant amount of metabolic heat, as much as five times the norm, and with the blood to the surface of the body greatly constricted, the cooling blanket can only reduce the temperature of the patient very slowly, if at all. If the patient has fever and thus an elevated set point temperature, and thus shivers at a temperature above normothermia, it has been found that cooling blankets are often unable to reduce the patient's temperature even to normothermia.

Additionally, because the heat transfer from the surface to the core of a patient by the application of cooling blankets is slow and inefficient, the control of the patient's core temperature by surface cooling is very difficult, if not impossible. The temperature of the patient tends to "overshoot" the desired low temperature, a potentially catastrophic problem when reducing the core temperature of a patient, especially to moderate or sever levels. Speedy adjustment of core temperature by surface cooling is difficult or even impossible, particularly if precise control is needed.

As is the case with the use of CPB machinery to warm blood removed from the body and replace it into the body, by-pass may be fast and control may be relatively precise, especially if large volumes of blood are being pumped through the system very quickly. However, as was previously stated, this method is complex, expensive, invasive and generally damaging to the blood, particularly if continued for any significant period of time.

Besides intentionally induced hypothermia or hyperthermia, it is sometimes desirable to control a patient's temperature to maintain the patient at normothermia, that is normal body temperature of about 37° C. For example, in a patient under general anesthesia, the body's normal thermoregulatory centers and mechanisms may not be fully functioning, and the anesthesiologist may wish to control the patient's body temperature by directly adding or removing heat. Similarly, a patient may lose an extraordinary amount of heat to the environment, for example, during major surgery, and the patient's unaided body may not be able to generate sufficient heat to compensate for the heat lost. This is especially true where, as a result of the anesthesia used during surgery, the patient's normal thermoregulatory response is reduced or eliminated. A device and method for controlling body temperature by adding or removing heat to maintain normothermia, would be desirable.

Additionally, a patient may suffer disease or trauma or have certain substances introduced into its body that cause an increased set point temperature resulting in fever, as in the case of infection or inflammation. The unaided body may then act to maintain a temperature above 37° C. and surface cooling may be ineffective in combating the body's thermoregulatory activity and reestablishing normothermia. Where, for example in stroke, the presence of fever has been found to correlate with very negative outcome, it may be very desirable to maintain normothermia.

The mammalian body generally functions most efficiently at normothermia. Therefore maintaining hypothermia in a portion of the body such as the brain or heart while maintaining the temperature of the rest of the body at normothermia may provide for protection of the target tissue, e.g. neuroprotection of the brain or protection of the myocardium while allowing the rest of the body to function at normothermia.

For the foregoing reasons, there is a need for a means to add or remove heat from the body of a patient in an effective and efficient manner, while avoiding the inadequacies of surface heat exchange and the dangers of CPB methods that require pumping the blood from the body of the patient, heating or cooling the blood, and then returning it to the patient. There is the need for a means of rapidly, efficiently and controllably exchanging heat with the blood of a patient so the temperature of the patient or target tissue within the patient can be altered, or maintained at some target temperature.

SUMMARY OF THE INVENTION

The present invention provides a heat exchange catheter having a heat exchange portion that comprises multiple heat exchange elements (e.g., discrete members such as tubes or filaments), and a method of heating or cooling the body of a patient by placing the heat exchange portion of such catheter into the bloodstream of the patient and exchanging heat with the bloodstream at a sufficient rate and for a sufficient length of time to alter the temperature of the patient.

Further in accordance with the invention, a heat exchange catheter of the invention may comprise a flexible catheter body or shaft having a proximal end and a distal end, the distal end of such catheter shaft being adapted to be inserted percutaneously into the vasculature or body cavity of a mammalian patient. A heat exchange region is provided on the catheter shaft, comprising a plurality of fluid impermeable heat exchange elements each having a length and opposed ends, each element being attached on at least one of the ends to the catheter shaft. When inserted in a blood vessel or other body cavity, body fluid can surround each heat exchange element. The shaft of the catheter preferably includes a fluid circulation path or lumen, and each heat exchange element preferably is attached at both ends to the shaft and incorporates a fluid circulation path or lumen that is in fluid communication with the fluid circulation path or lumen of the catheter shaft. In this manner, heat exchange fluid may be circulated into or through the individual heat exchange elements as they are circumferentially surrounded by the body fluid. Alternatively, the individual heat exchange elements may incorporate cul-de-sac filaments, and may thus be attached to the catheter shaft at only one end.

Further in accordance with some embodiments of the invention, the heat exchange region may be less than one-half the length of the catheter shaft and may be located at or near the distal end thereof. In such embodiments, an insulating region may be formed on the catheter shaft proximal to the heat exchange region to reduce unwanted transfer of heat to and from the proximal portion of the catheter shaft.

Further in accordance with the present invention, there is provided a system for heat exchange with a body fluid, the system including a) a liquid heat exchange medium and b) a heat exchange catheter having a plurality of discrete, elongate heat exchange elements. The catheter includes a shaft having a proximal end and a distal end, the distal end being adapted to be inserted percutaneously into a body cavity. The shaft having a circulation pathway therein for the circulation of heat exchange medium therethrough. The discrete heat exchange elements are attached to the catheter so that when the catheter is inserted in the body cavity, body fluid surrounds each element.

The system further may include a sensor or sensors attached to or inserted into the patient to provide feedback on the condition of the patient, for example the patient's temperature. The sensors are desirably in communication with a controller that controls the heat exchange catheter based on the feedback from the sensors.

Still further in accordance with the present invention, there is provided a method for exchanging heat with a body fluid of a mammal. The method includes the steps of a) providing a catheter that has a circulatory fluid flow path therein and a heat exchange region thereon, such heat exchange region including heat (exchange elements that are attached to the catheter shaft at the heat exchange region, b) inserting the catheter into a body cavity and into contact with a body fluid, the heat exchange elements thus being surrounded by the body fluid and c) causing a heat exchange medium to flow through the circulatory flow path of the catheter so that the medium exchanges heat with a body fluid through the heat exchange elements. Each of the heat exchange elements may be hollow, and step C of the method may include causing heat exchange fluid to flow through the hollow heat exchange elements.

It is an object of this invention to provide an effective means for adding heat to a patient suffering from hypothermia.

It is a further object of this invention to provide an effective means for removing heat from the bloodstream of a patient suffering from hyperthermia.

It is a further object of this invention to provide an effective means of adding or removing heat from a patient to induce normothermia.

It is a further object of this invention to provide an effective means for maintaining normothermia.

It is a further object of this invention to provide an effective means of cooling a patient to a target temperature and controllably maintaining that temperature.

It is a further object of this invention to provide a cooling catheter that has an advantageous configuration.

It is a further object of this invention to cool a target region of a patient.

It is a further object of this invention to maintain a patient at a target temperature.

It is a further object of this invention to provide a heat exchange catheter that is configured to efficiently exchange heat with the blood of a patient while allowing continued flow of the blood past the catheter with a minimum of restriction to that blood flow.

It is a further object of this invention to provide a heat exchange catheter having multiple heat exchange balloons.

It is a further object of this invention to provide a heat exchange catheter having a heat exchange portion that comprises multi-filaments.

It is a further object of this invention to provide a heat exchange catheter having an insulated shaft.

It is a further object of this invention to provide an effective method of controlling the temperature of a body fluid.

It is a further object of this invention to provide an effective method of warming a body fluid.

It is a further object of this invention to provide an effective method of cooling a body fluid.

It is a further object of this invention to provide an effective method for inducing hypothermia.

BRIEF DESCRIPTION OF THE DRAWINGS

FIG. 8 is elevational view of alternative embodiment of a heat exchange catheter of the present invention having a proximal insulating region, and a distal heat exchange region;

FIG. 8A is a sectional view of an insulating region of the catheter of FIG. 8, taken along line 8A—8A, with standoffs interposed between a central fluid delivery shaft and an outer balloon;

FIG. 8B is a sectional view similar to FIG. 8A of an alternative configuration of an insulating region with a plurality of inflatable spacers between the central fluid delivery shaft and an outer sleeve;

FIG. 9 is an elevational view of a distal portion of an alternative embodiment of a heat exchange catheter of the present invention having a plurality of flexible heat exchange elements connected at one end to the catheter;

FIG. 9A is a sectional view of a heat exchange element of the catheter of FIG. 9 having a fluid circulation path therein, taken along line 9A—9A;

FIG. 13 is a sectional view through an alternative heat exchange catheter of the present intention having a plurality of flexible heat exchange elements connected at one end to the catheter adapted for fluid flow therethrough;

FIG. 14 is a sectional view through one of the flexible heat exchange elements shown in FIG. 13, taken along line 14—14;

FIG. 19 is a plan view of the faceplate of the proximal manifold of the heat exchange catheter taken along line 19—19 of FIG. 16;

FIG. 20 is a plan view of the divider plate of the proximal manifold of the heat exchange catheter shown at 20—20 of FIG. 16;

FIG. 25 is a plan view of the faceplate of the proximal manifold of the heat exchange catheter taken along line 25—25 of FIG. 22; and FIG. 26 is a plan view of the divider plate of the proximal manifold of the single loop heat exchange catheter taken along line 26—26 of FIG. 22.

DESCRIPTION OF THE PREFERRED EMBODIMENTS

The present invention provides an improved heat exchange catheter that provides increased surface area for heat transfer with the respective body fluid without increasing the overall cross-sectional size of the catheter. Although the present invention is primarily intended to be used in the bloodstream for regulating the patient's blood temperature, those of skill in the art well understand that various other applications for the catheter of the present invention are possible. Indeed, the present invention may have applications beyond controlling the temperature of an internal body fluid, and the claims should not be so limited.

In a preferred application, one or more of the catheters of the present invention are positioned within a patient's vasculature to exchange heat with the blood in order to regulate the overall body temperature, or to regulate the temperature of a localized region of the patient's body. The catheter of the present invention may be, for example, suitable for exchanging heat with arterial blood flowing toward the brain to cool the brain, and may thus prevent damage to brain tissue that might otherwise result from a stroke or other injury, or cooling venous blood flowing toward the heart to cool the myocardium to prevent tissue injury that might otherwise occur following an Ml or other similar event.

Figure 1:
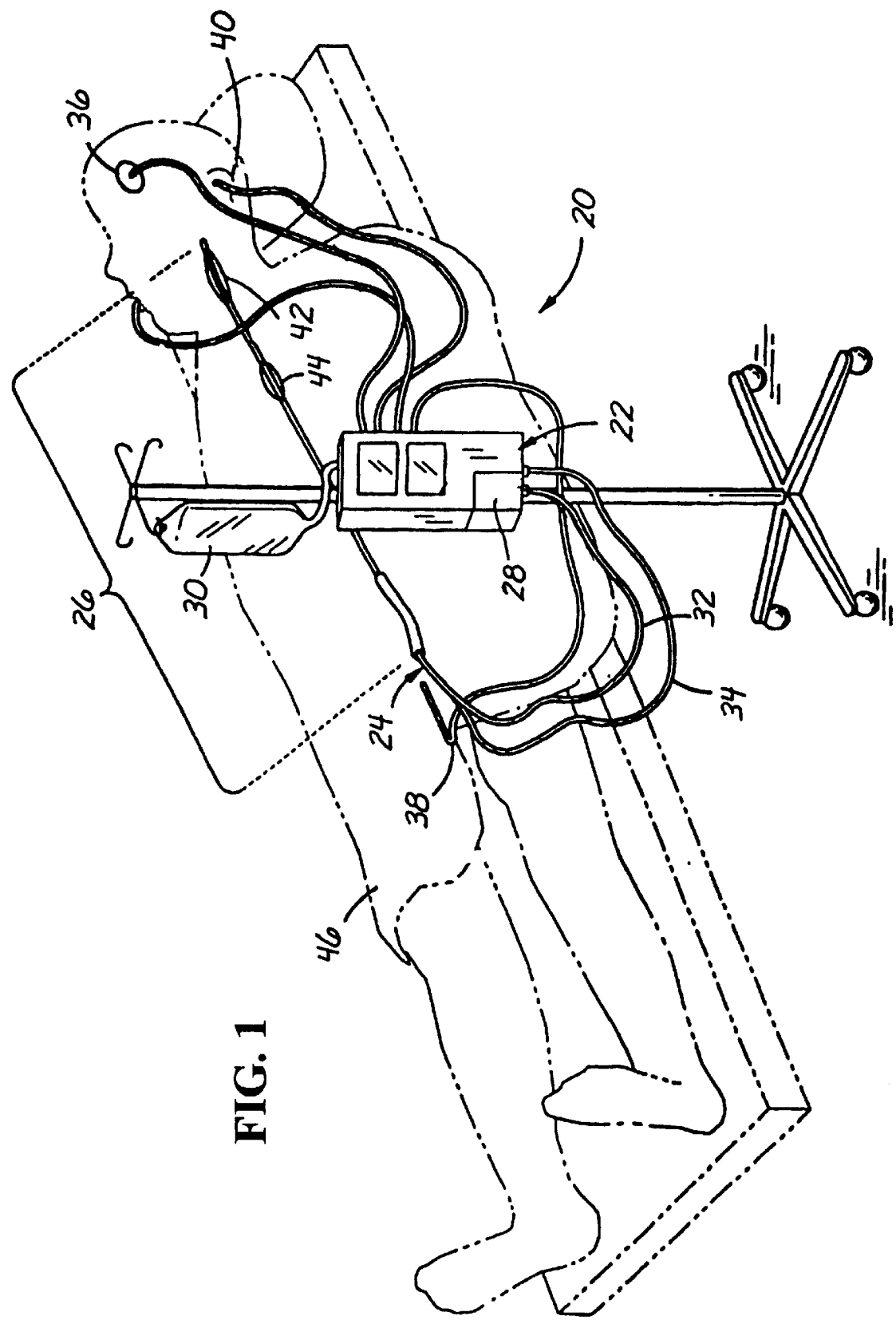
FIG. 1 is a perspective view of a patient undergoing treatment using a system in accordance with the present invention.

The heat exchange catheters disclosed herein may be utilized in a heat exchange system suitable for regulating the temperature of a patent or a region of the patient's body. One example of such a heat exchange catheter system 20 utilizing any of the catheters disclosed herein is shown in FIG. 1. The system 20 may include a catheter control unit 22 and a heat exchange catheter 24 formed with at least one heat transfer section 44. The heat transfer section or sections are located on that portion of the catheter 24, as illustrated by section 26, that is inserted into the patient. This insertion portion is less than the full-length of the catheter and extends from the location on the catheter just inside the patient, when the catheter is fully inserted, to distal end of the catheter. The catheter control unit 22 may include a fluid pump 28 for circulating a heat exchange fluid or medium within the catheter 24, and a heat exchanger component for heating and/or cooling circulating fluids within the heat transfer system 20. A reservoir or fluid bag 30 may be connected to the control unit 22 to provide a source of heat transfer fluid such as, saline, blood substitute solution, or other biocompatible fluid. A circulatory heat exchange flow channel within the catheter may be respectively connected to inlet 32 and outlet 34 conduits of the pump 28 for circulation of the heat transfer fluid to cool the flow of fluid within a selected body region. A similar arrangement may be implemented for heating of selected body regions simultaneously or independently from the cooling component of the system.

The control unit 22 may further receive data from a variety of sensors which may be, for example, solid-state thermocouples to provide feedback from the catheter and various sensors to provide patient temperature information representing core temperature or temperature of selected organs or portions of the body. For instance, sensors may include a temperature probe 36 for the brain or head region, a rectal temperature probe 38, an ear temperature probe 40, an esophageal temperature probe (not shown), a bladder temperature probe (not shown), and the like.

Based upon sensed temperatures and conditions, the control unit 22 may direct the heating or cooling of the catheter in response. The control unit 22 may activate a heat exchanger at a first sensed temperature, and may also de-activate the heat exchanger at a second sensed temperature which may be relatively higher or lower than the first sensed temperature or any other predetermined temperature. The control unit 22 may of course independently heat or cool selected heat transfer sections to attain desired or preselected temperatures in body regions. Likewise, the controller 22 may activate more than one heat exchanger to control temperature at particular regions of the patient's body. The controller might also activate or de-activate other apparatus, for example external heating blankets or the like, in response to sensed temperatures. The regulation exercised over the heat transfer catheters or other devices may be a simple on-off control, or may be a significantly more sophisticated control scheme including regulating the degree of heating or cooling, ramp rates of heating or cooling, proportional control as the temperature of the heat exchange region or patient approaches a target temperature, or the like.

The catheter control unit 22 may further include a thermoelectric cooler and heater (and associated flow conduits) that are selectively activated to perform both heating and cooling functions with the same or different heat transfer mediums within the closed-loop catheter system. For example, a first heat transfer section 42 located on the insertion portion 26 of at least one temperature regulating catheter 24 may circulate a cold solution in the immediate head region, or alternatively, within a carotid artery or other blood vessel leading to the brain. The head temperature may be locally monitored with temperature sensors 36 positioned in a relatively proximate exterior surface of the patient or within selected body regions. Another heat transfer section 44 of the catheter 24 also located on the insertion portion 26 may circulate a heated solution within a collapsible balloon or otherwise provide heat to other body locations through heat elements or other mechanisms described in accordance with other aspects of the invention. While heat exchange catheter 24 may provide regional hypothermia to the brain region for neuroprotective benefits, other parts of the body may be kept relatively warm so that adverse side effects such as discomfort, shivering, blood coagulopathies, immune deficiencies, and the like, may be avoided or minimized. Warming of the body generally below the neck may be further achieved by insulating or wrapping the lower body in a heating pad or blanket 46 while the head region above the neck is cool. It should be understood of course that multiple heat exchange sections of the catheter 24 may be modified to provide whole body cooling or warming to affect body core temperature.

Figure 2:
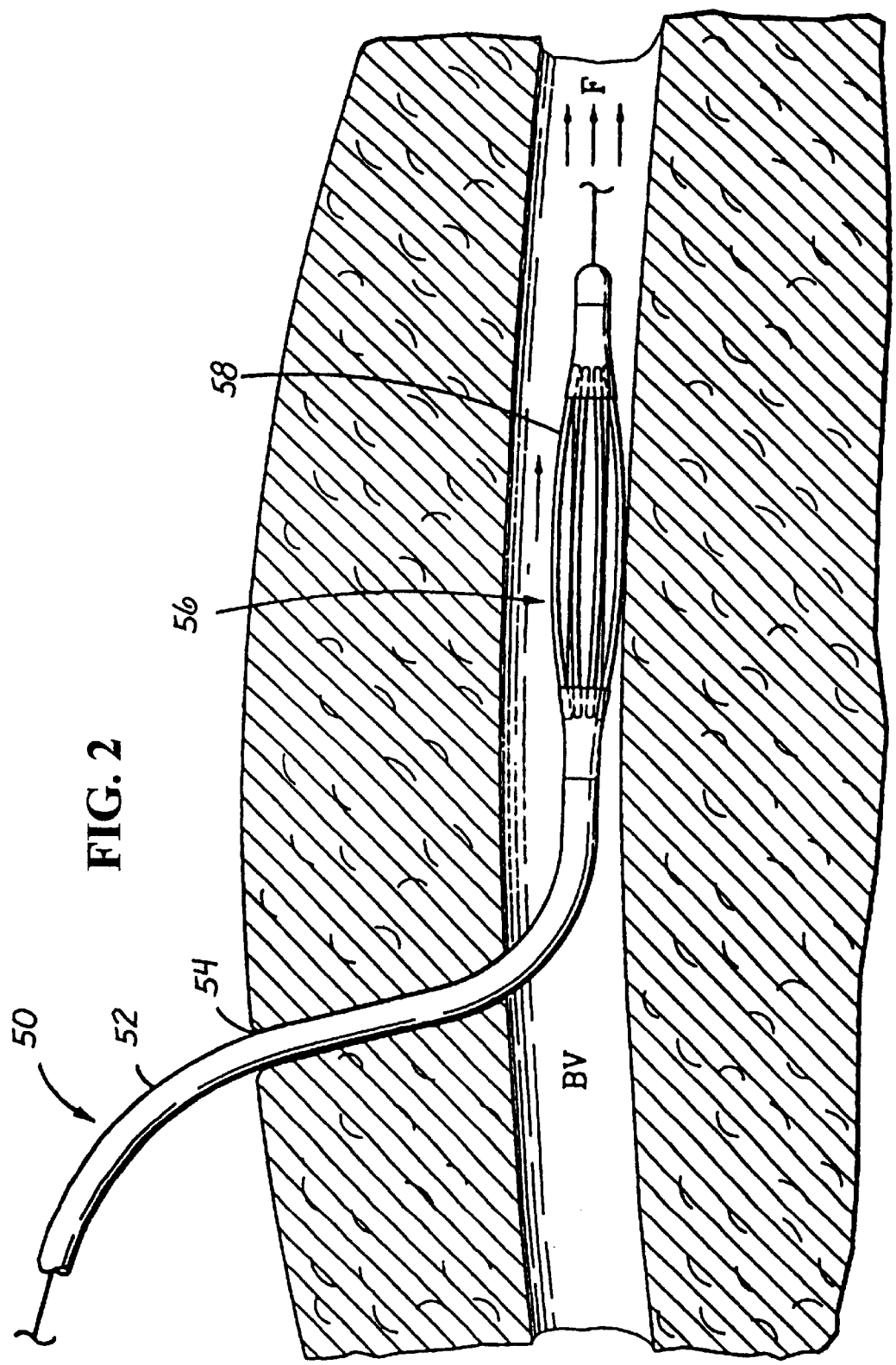
FIG. 2 is a sectional view of a vessel of a patient showing one embodiment of a heat exchange catheter of the present invention inserted therein.

FIG. 2 illustrates one particular heat exchange catheter 50 of the present invention inserted into a body cavity, in this case a blood vessel BV. The blood flow F is indicated by the arrows directed to the right. The heat exchange catheter 50 includes an elongate shaft 52 adapted to extend through a puncture wound 54 into the blood vessel BV. The catheter 50 has a proximal end that remains outside the body and a distal end that is inserted into the body cavity.

A heat exchange region 56 is provided along a distal portion of the catheter 50 which is immersed in the bloodstream. The heat exchange region 56 corresponds to either of the heat exchange regions 42 or 44 described above with respect to FIG. 1. The illustrated embodiment is shown in more detail in FIGS. 3–6, and includes a plurality of heat exchange elements 58 attached to the catheter shaft 52 providing enhanced heat exchange with the blood, as will be described. Any of the other embodiments disclosed in the present application may be substituted in the heat exchange region 56.

Figure 3:
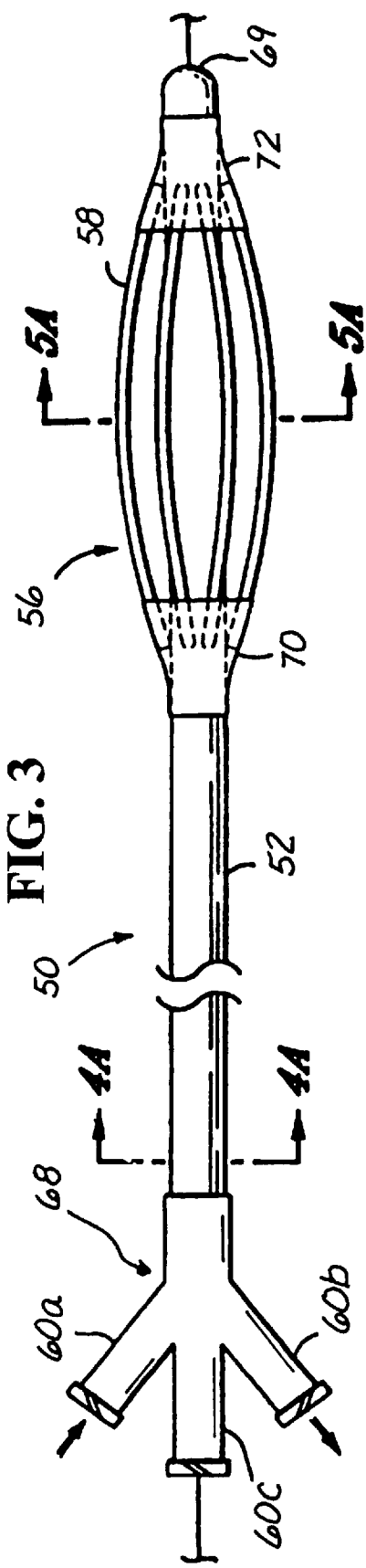
FIG. 3 is an elevational view of an exemplary embodiment of a heat exchange catheter of the present invention having multiple hollow discrete elements for flowing heat transfer medium therethrough on a distal portion of the catheter.

With reference to FIG. 3, the heat exchange catheter 50 comprises the aforementioned elongate shaft 52 having a heat exchange region 56 on a distal end, and being provided with a plurality of ports 60 on a proximal end. In particular, the catheter 50 includes a fluid inlet port 60a, a fluid outlet port 60b, and a guide wire insertion port 60c.

Figure 4B:
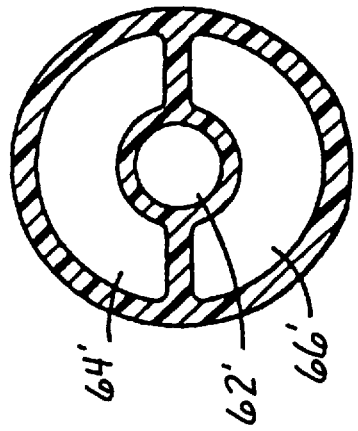
FIG. 4B is a sectional view similar to FIG. 4A of an alternative catheter.
Figure 4A:
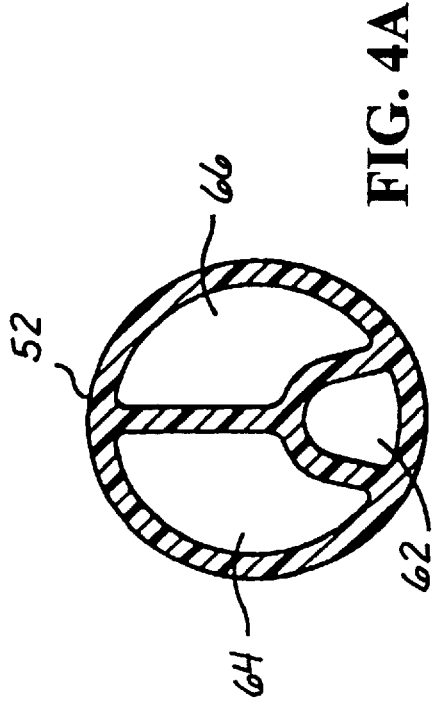
FIG. 4A is a sectional view of a proximal end of the catheter of FIG. 3 taken along line 4A—4A.

FIG. 4A illustrates a cross-section of the elongate shaft 52 taken along the line 4A—4A in FIG. 3, wherein three lumen are provided within the shaft. A guide wire lumen 62 is located generally between two heat transfer fluid circulation lumen 64 and 66. One circulation lumen 64 is in fluid communication with the fluid inlet port 60a, and the other circulation lumen 66 is in fluid communication with the fluid outlet port 60b. It may be readily determined, however, that if flow in the opposite direction is desired, for example to achieve counter-current flow with the blood as described below, either lumen may function as inflow lumen with the other lumen functioning as the outflow lumen. The direction of flow may thus be easily and satisfactorily reversed.

FIG. 4B illustrates an alternative cross-section of the elongate shaft 52 wherein a centrally disposed guide wire lumen 62' is located between two heat transfer fluid circulation lumen 64' and 66'.

The cross-sectional configuration of the shaft 52 desirably extends from a junction with a hub 68 to the distal end 69 of the catheter. Alternatively, the extreme distal portion may consist of just the guide wire lumen or an extension thereof. The view in FIG. 3 is somewhat abbreviated as indicated by the break lines, and the catheter 50 of this embodiment may be anywhere from 60 to 50 cm in length.

The heat exchange region 56 begins at an outlet manifold 70 and ends at an inlet manifold 72 disposed distally therefrom. A plurality of the aforementioned heat exchange elements 58 extend adjacent to and generally in parallel with the shaft 52 between the inlet and outlet manifolds 70, 72. Each element 58 is attached on at least one of its ends to the heat exchange region 56 and at least a portion of its length is transversely spaced from the shaft 52 so that when inserted in a fluid body cavity having body fluid therein, the body fluid circumferentially surrounds each heat exchange element. The term "circumferentially surrounds" is not meant to imply that the cross-section of each heat exchange element 58 is circular, but instead means that when viewed in transverse cross-section, each element is peripherally surrounded by body fluid. This greatly increases the effective heat transfer surface area of the catheter 50 and facilitates heat exchange with the body fluid.

Figure 5A:
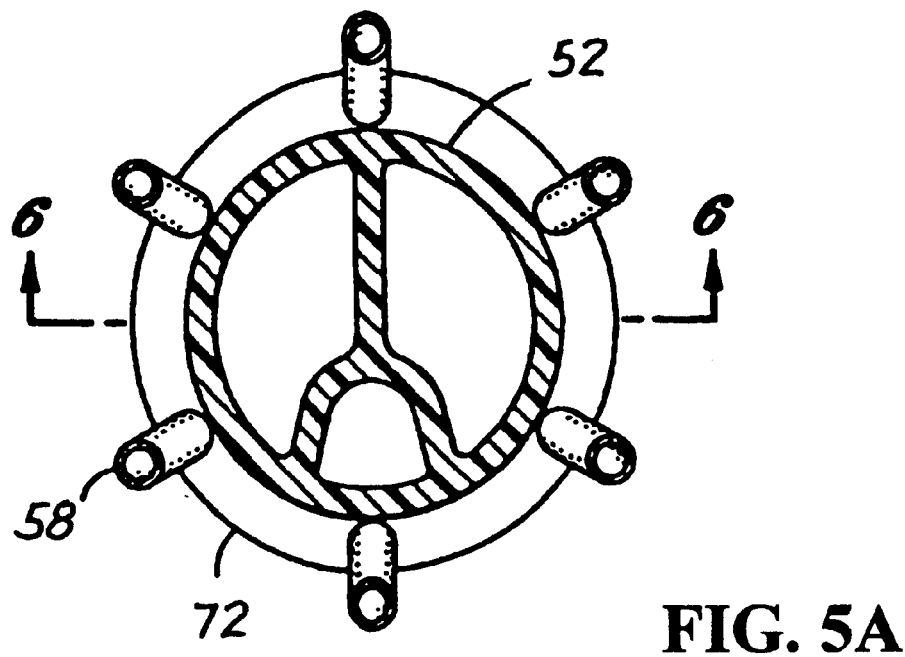
FIG. 5A is sectional view of the distal heat transfer portion of the catheter of FIG. 3, taken along line 5—5, and showing six heat exchange elements.
Figure 5B:
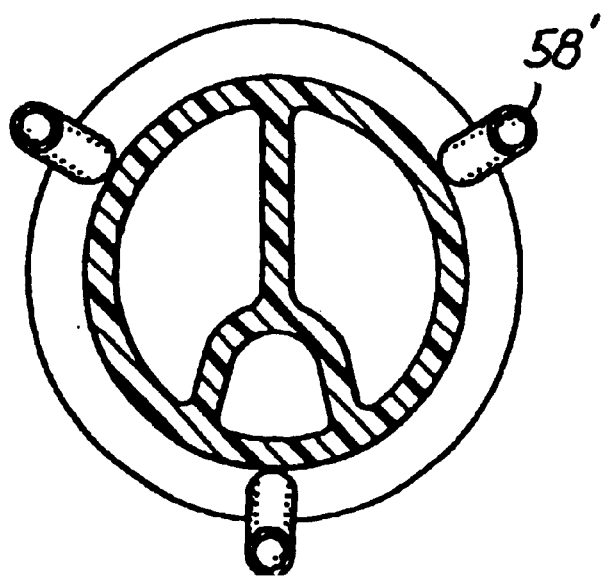
FIG. 5B is a sectional view, similar to FIG. 5A, of an alternative heat transfer portion of the catheter having three heat exchange elements.

As seen in cross-section in FIG. 5A, there are six such heat exchange elements 58 distributed uniformly around the circumference of the catheter shaft 52. As will be appreciated from the following discussion, improved heat exchange using the catheter 50 of the present invention can be accomplished with as few as two heat exchange elements 58. For example, FIG. 5B illustrates an alternative embodiment with three heat exchange elements 58'. As illustrated, the heat exchange elements 58 are distributed evenly around the circumference of the shaft 52, but other configurations such as that shown in FIG. 8 are possible.

Figure 6:
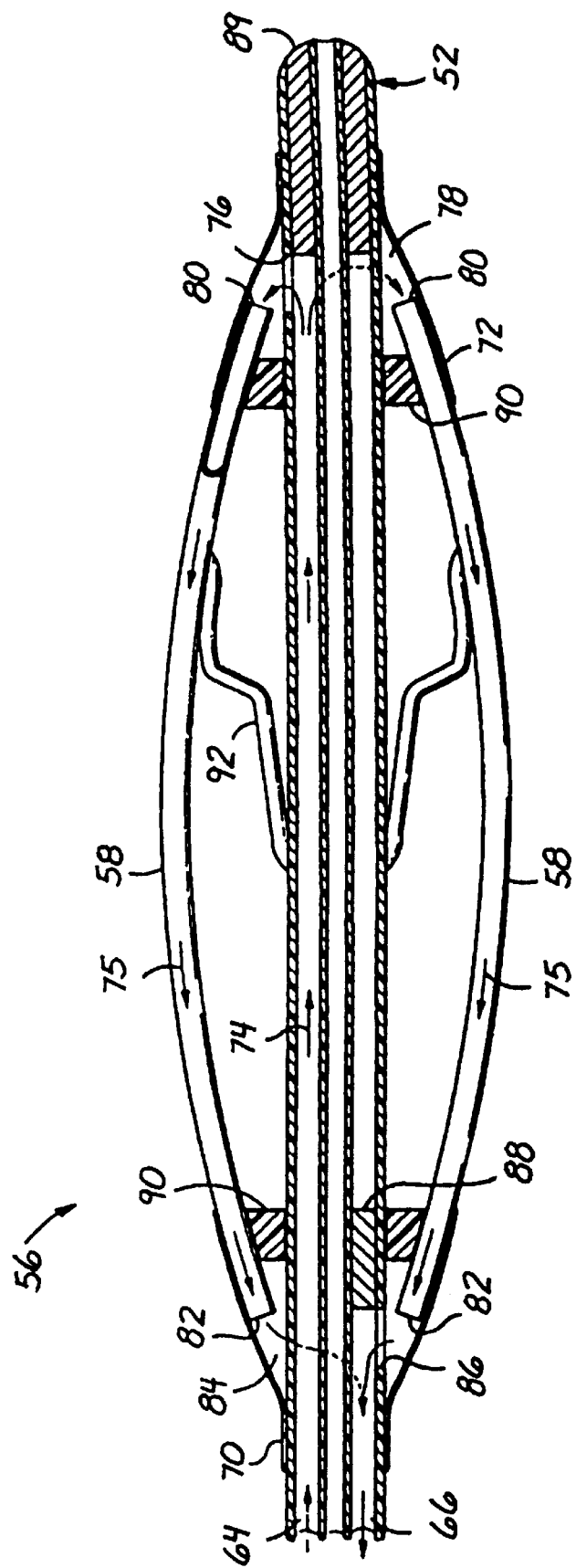
FIG. 6 is a longitudinal sectional view through the distal heat transfer portion of the catheter of FIG. 3 taken along line 6—6 of FIG. 5A.

The heat exchange catheter 50 of the present invention provides a circulatory fluid flow path therein, as best seen in FIG. 6. In the illustrated embodiment, the circulatory fluid flow path extends through the elongated heat exchange elements 58. In FIG. 6, the upper lumen 64 functions as a heat exchange medium inflow lumen. The lower lumen 66 functions as a heat exchange medium outflow lumen. If the direction of heat transfer fluid flow in the heat exchange elements is desired to be in the opposite direction from that illustrated here, however, it may be readily accomplished by reversing the function of these two lumen.

The circulatory flow path in the heat exchange region 56 of the catheter 50 is illustrated in FIG. 6 by the flow arrows 74 and 75. Specifically, the exchange medium travels distally through the inflow lumen 64 until it reaches a port 76 which is in fluid communication with an interior space 78 defined within the inlet manifold 72. Each of the heat exchange elements 58 is desirably formed as a hollow tube having an inflow orifice 80 in fluid communication with the interior space 78. In like manner, each heat exchange element 58 has an outflow orifice 82 that is in fluid communication with an interior space 84 defined within the outlet manifold 70. The outflow lumen 66 has a port 86 that receives heat exchange medium exiting from the outflow orifices 82. A plug member 88 provided in the outflow lumen 66 prevents heat exchange medium from continuing distally past the outlet manifold 70, while plug members 89 close the distal ends of lumen 64 and 66. To reiterate the circulatory flow path, heat exchange medium travels distally (arrow 74) through inflow lumen 64 to exit through the port 76, enters the space 78 within the inlet manifold 72, travels within the space to enter the inflow orifices 80 of each of the heat exchange elements 58, travels proximally (arrows 75) through the heat exchange elements, flows from the outflow orifices 82 into the space 84 formed within the outlet manifold 70, and enters the outflow lumen 66 through the port 86 which carries the medium back to the proximal end of catheter 50. Again, the heat transfer fluid flow through the heat exchange elements 58 could be in the distal or proximal direction and, depending on the catheter insertion technique, the flow could be con-current or counter-current to the blood flow direction.

The inlet and outlet manifolds 70, 72 may be formed by a variety of constructions, a flared, thin-walled jacket being shown. The manifolds 70, 72 transition on one end to meet the exterior of the shaft 52, and are sealed thereto. On the opposite end, the open area within each manifold receives the ends of the heat exchange elements 58, and a potting compound 90 which may be a suitable adhesive, seals the interior spaces 78 and 84 from the exterior of the circulatory flow path. The heat exchange elements 58 are thus sealed between the respective manifolds 70, 72 and the potting compound in a fluid tight manner. Of course, other constructions such as a molded polymer or shrink-wrap material may be substituted for the flared jacket, and other constructions such as a sealing ring may be substituted for the potting compound.

The heat exchange elements 58 are illustrated as being bowed outward slightly from the catheter shaft 52. This arrangement ensures that the elements 58 are surrounded by body fluid during use, such as seen in FIG. 2, so as to greatly enhance heat transfer capacity for a given fluid flow rate. That is, the heat exchange medium is divided at the distal end of the catheter and flows proximally through a plurality of parallel paths, each of which passes through heat exchange elements 58 each having a continuous external surface. This arrangement is best illustrated in FIGS. 5A and 5B. In addition, some heat exchange takes place between the inflow lumen 64 and the external body fluid, through the wall of the shaft 52.

One means of ensuring separation between heat exchange elements 58 and shaft 52 is to provide a spring member therebetween, such as that shown at 92 in FIG. 6. A spring member 92 is desirably connected to a radially inner portion of each heat exchange element 58 and is cantilevered toward and into contact with the shaft 52. During insertion of the catheter 50, external forces may cause the heat exchange elements 58 to be pressed inward, compressing the spring member 92 which slides against the shaft 52. Upon placement in the appropriate body cavity, the spring member 92 expands to move the heat exchange elements 58 radially outward into optimum heat exchange position. Advantageously, the spring members 92 have a relatively low profile in the blood flow path, and thus minimize any obstruction to blood flow.

Another construction that would assure separation in use between the heat exchange elements 58 and shaft 52 is to provide thin-walled, inflatable tubes as the heat exchange elements. The elements are slightly longer than the distance between the inlet and outlet manifolds, 70, 72. When the elements 58 are collapsed, for example upon insertion into the patient, they will fold down flat against the shaft to provide a low profile. When they are inflated, for example by pressurized and flowing heat exchange fluid in use, they will bow out away from the shaft. See, for example, FIG. 3 and FIG. 8. Alternatively, the distance between the inlet and outlet manifolds 70, 72 may be variable via a pull-wire (not shown) or other such expedient that acts on the shaft 52. For example, the shaft 52 may be constructed in telescoping sections, or may be bendable, so that the distance between the inlet and outlet manifolds 70, 72 can be shortened upon actuation of the pull-wire. In this manner, the elements 58 initially lie flat against the elongated shaft 52 but are then caused to bow outward away from the shortened shaft.

Another advantage of providing a plurality of flexible heat exchange elements, such as shown at 58, is that the cross-sectional profile of the heat exchange region 56 easily conforms to tortuous body cavities. That is, as best seen in FIG. 5A, the circumferential gaps provided between each of the individual heat exchange elements 58 permits them to shift radially and circumferentially so that they may be more bunched on one side or the other. This capacity to shift position greatly enhances the ability of placing heat exchange region 56 into tight or tortuous body cavities and in activating the flow of heat exchange fluid to expand the heat exchange elements without undue restriction of blood flow around the heat exchange region. It has been found that adequate flow in the blood vessel may generally be retained if the heat exchange elements obstruct 50% or less of the cross-sectional area of the vessel.

Figure 7:
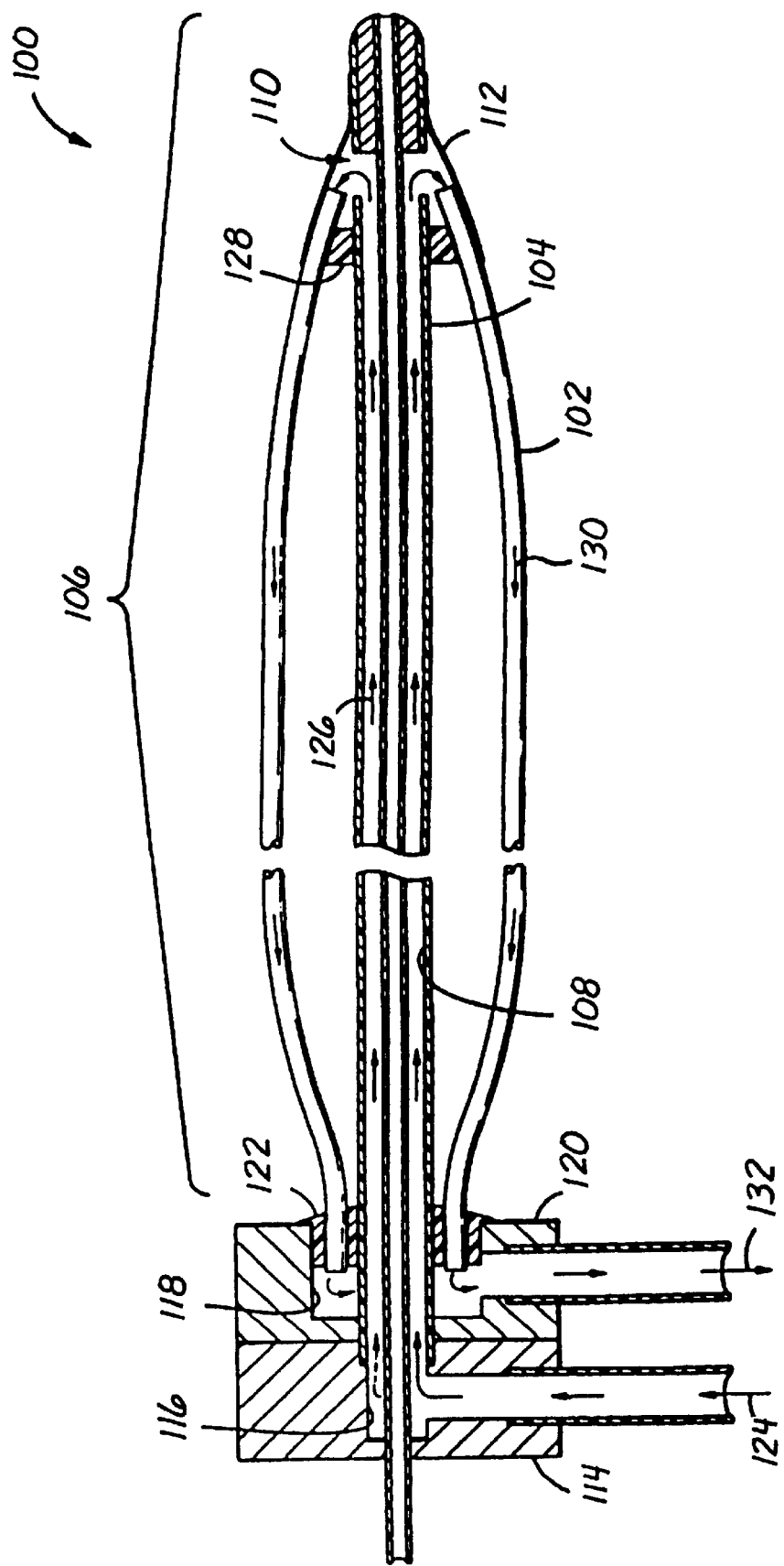
FIG. 7 is a longitudinal sectional view through an alternative embodiment of a heat exchange catheter of the present invention having multiple hollow discrete elements for flowing heat transfer medium therethrough disposed along the entire length of the catheter.

An alternative embodiment of a heat exchange catheter 100 of the present invention is seen in FIG. 7. The catheter 100 is similar to the catheter 50 described previously in that a heat exchange medium circulation path is provided therein, and a plurality of elongated heat exchange elements 102, discrete from a catheter shaft 104, form a portion of the circulation path. In the embodiment of FIG. 7, however, the heat exchange region 106 extends along the entire length of the catheter shaft 104.

Each of the heat exchange elements 102 is preferably formed as an elongate hollow filament. The heat exchange catheter 100 includes a fluid circulation path therein comprising an inner lumen or lumen 108 formed within the inner shaft 104, a space 110 formed within a manifold 112 provided at the distal end of the catheter, and the hollow lumen of the heat exchange elements 102 are in fluid communication with that space 110. The proximal end of the inner shaft 104 fits within an inlet fitting 114 having an inner chamber 116 that communicates with the lumen 108. The inner shaft 104 extends through a chamber 118 formed in an outlet fitting 120, and the proximal ends of the heat exchange elements 102 are sealed in the fluid communication with the chamber 118 using potting compound 122. In this manner, fluid entering the chamber 116, as indicated with arrow 124, is directed into the lumen 108 and travels distally through the catheter 100 as indicated by arrows 126. At the distal manifold 112, the fluid is redirected 180 degrees into the hollow lumen of the heat exchange elements 102. Again, potting compound 128 is used seal the distal ends of the elements 102 within the space 110. The fluid travels proximally through the elements 102, as indicated by arrows 130, and exits the heat exchange elements into the chamber 118 to be removed from the chamber as indicated by arrow 132.

The advantage of providing a heat-exchange region 106 along the entire length of catheter 100 is the capacity for greater heat exchange with the body fluid. In addition, the catheter 100 having a heat exchange region 106 along 100 percent of its length may more effectively provide whole body heating or cooling. Furthermore, in the previously described catheter, some heat might be transferred to or from the body fluid through the proximal portion of the catheter that is not part of the heat-exchange region. In the embodiment of FIG. 7, on the other hand, the entire catheter is designed to exchange heat with the body fluid.

FIG. 8 illustrates a further embodiment of a heat exchange catheter 150 having a heat exchange region 152 on its distal portion, and an insulating region 154 on its proximal portion. In the illustrated embodiment, the heat exchange region 152 and insulating region 154 are approximately equal in length, both being about 50 percent of the entire length of the catheter 150. In a preferred embodiment, the insulating region 154 is substantially longer than the heat exchange region 152, and preferably at least 75 percent of the length of the catheter 150. Desirably, the combined length of the heat exchange region 152 and insulating region 154 is approximately equal to the entire length of the catheter 100. One specific example is an insulating region that extends about 85–90% of the total catheter length, and a heat exchange region that extends the remaining 10–15%. Of course, various alternative configurations are contemplated, including intermittent and interspersed insulating and heat exchange regions.

As before, the catheter 150 in FIG. 8 includes a heat exchange medium inlet port 160 and a heat exchange medium outlet port 162. A fluid circulation path (not shown) is provided within an elongate shaft 164. A plurality of elongated heat exchange elements 166 are provided parallel to but spaced from the shaft 164 in the heat exchange region 152. Preferably, the heat exchange elements 166 are hollow filaments that form separate parts of the fluid circulation path within the catheter 150. To this end, a distal manifold 168 receives the distal ends of the heat exchange elements 166, and a proximal manifold 170 receives the proximal ends. The manifolds 168, 170 define fluid flow spaces therein; a space within the distal manifold 168 being in fluid communication with the inlet port 160, and a space within the proximal manifold 170 being in fluid communication with the outlet port 162. In this manner, a liquid heat exchange medium flows into the port 160 and to the distal end of the catheter 150 before returning to the outlet port 162 via the hollow heat exchange elements 166.

The insulating region 154 includes an insulating member 172 disposed longitudinally about the shaft 164. The insulating member 172 may be a variety of constructions, including a solid sleeve or a fluid-filled balloon. In a preferred embodiment, the insulating member 172 comprises an inflatable balloon having an interior space in communication with an inflation port 173. A suitable insulating fluid, such as nitrogen gas or carbon dioxide gas, inflates the balloon 172 away from the side of the shaft 164. In this manner, even if the entire length of the shaft 164 is immersed in a body fluid, only the heat exchange region 152 transfers heat efficiently to or from the body fluid.

As seen in FIG. 8A, the shaft 164 may be centered within and held spaced from the insulating member 172, for example by collapsible stand-offs 175, to prevent the shaft from resting against the side of the inflated insulating member and comprising the insulating capacity of the insulating member. The stand-offs 175 maybe relatively thin and flexible so that when the insulating member is collapsed for insertion and removal, they fold down against the shaft without adding significantly to the overall catheter profile.

Alternatively, as shown in FIG. 8B, the insulating member could be a multi-lumen, thin-walled balloon with a central lumen into which the shaft 164 is inserted, and inflatable insulating lumens 179 surrounding the central lumen. An insulating sleeve 181 may surround the entire insulating region.

The configuration of FIG. 8 having an insulating region and a heat transfer region may be particularly useful in cooling blood flowing to the brain to regionally direct the cooling effect of the catheter. The effectiveness of cooling or heating the blood depends in part upon the difference in temperature between the surface of the heat exchange region in contact with the blood, and the temperature of the blood. This difference in temperature is referred to herein as $\Delta T$. The catheter 150 can be inserted in, for example the femoral artery, passed through the vasculature, for example up the aorta, so that the heat exchange region 152 is located in the carotid artery. The heat exchange fluid is circulated through the catheter 150, and remains cool until it reaches the heat exchange region 152 by virtue of the insulating region 154, and thus a maximum $\Delta T$ is maintained. Without the insulating region 154, the effectiveness of the heat exchange medium is diminished, and significantly less cooling of the blood at the desired location, in this case the carotid artery, may result.

Additionally, the regional effect of the cooling may also be compromised by the exchange of heat with blood that does not subsequently circulate to the desired region of the body. In the example above of regionally cooling the brain, the insulating region 154 prevents the cold heat exchange fluid from exchanging heat with the blood within the arterial system in the femoral artery and the ascending aorta, which blood would circulate to the trunk and legs of the patient. This cooling of blood which then circulates to other regions of the body can result in a general cooling of the entire body. While this general cooling may be desirable in some applications, it may be undesirable in other applications such as applications wherein it is intended to effect regional or localized cooling of the heart or the brain. In this regard, such general cooling can result in discomfort, such as shivering, in the patient, or other negative side effects of whole body hypothermia that might be avoided by regional cooling.

Up to now, the heat exchange elements have been described as hollow filaments forming a portion of a fluid flow path and attached at both ends to the catheter shaft. The present invention is of a more general nature, however, in that the multiple and distinct heat exchange elements need not be attached at both ends to the shaft, but may instead be constrained along a portion of its length with respect to the shaft so that a free end thereof is permitted to drift freely within the body fluid. The freely floating elements desirably define an internal "cul-de-sac" fluid flow path.

In particular, FIG. 9 illustrates a heat exchange catheter 180 in accordance with the present invention having an elongate shaft 182 and ;a plurality of heat exchange elements 184 attached thereto. The heat exchange elements 184 are attached at distal ends to the shaft 182 and are generally free-floating at distal tips 186. These elements 184 are preferably flexible and collapsible so as to compress against the exterior of the shaft 182 to provide a low profile during insertion and removal of catheter 180. In addition, the flexible nature of the elements 184 facilitates location in and passage through tortuous passages, and minimization of restriction to flow of blood through the vessels when inflated. It should be noted that the elements 184 along any one catheter 180 may be of different lengths. The catheter 180 further may include a proximal insulating member 188, which may be a single- or multi-lumen balloon as described above.

The heat exchange elements 184 can be provided in the variety of constructions. Each of the heat-exchange elements 184 may provide fluid circulation therein. The cross-sectional view of FIG. 9A illustrates the heat exchange element 184 having a fluid inlet path 190 and a parallel fluid outlet path 192. The fluid paths 190,192 are placed in fluid communication with a main circulation path provided within the shaft 182. In this manner, the heat exchange elements 184 are somewhat similar to the elements 58 described above with respect to the first embodiment, but are somewhat freer to float within the body fluid. In addition, the elements 184 being attached at only cone end permits them to more freely migrate around circumference of the shaft 182 when the catheter 180 is advanced through tortuous passage ways. A further embodiment of this nature is seen in FIGS. 13 and 14.

Figure 10A:
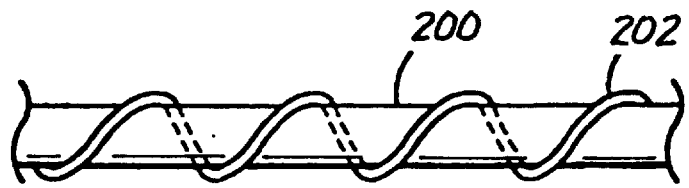
FIG. 10A is a detailed view of a portion of a discrete heat transfer element of the present invention having a helical fin thereon for enhanced heat transfer.
Figure 10B:
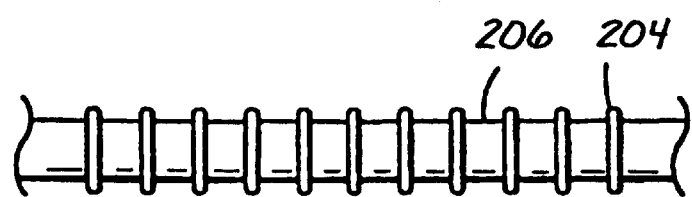
FIG. 10B is a detailed view of a portion of a discrete heat exchange element of the present invention having circumferential fins thereon for enhanced heat transfer.

To further facilitate heat exchange between the body fluid and the heat exchange elements described herein, each of the elements may be provided with a flow disrupting rib or other discontinuity. It is a well-known principle of heat exchange that reducing the laminar boundary layer around an object in a fluid flow path increases the potential heat transfer between that object and the fluid. Thus, for example, FIG. 10A illustrates a tubular heat exchange element 200 provided with a helical rib 202 thereon. Other such configurations are possible, including circumferentially oriented ribs 204 on a heat exchange element 206, as seen in FIG 10B.

Figure 11:
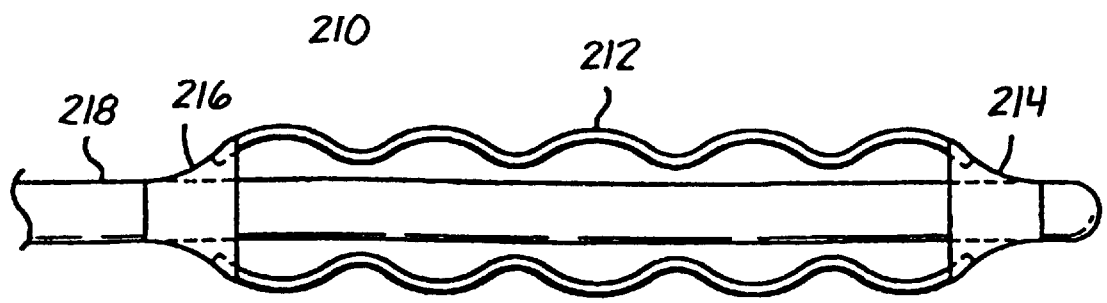
FIG. 11 is an elevational view of a distal portion of an alternative heat exchange catheter of the present invention having a plurality of undulating discrete elements for flowing heat transfer medium therethrough.

To still further facilitate heat transfer between the exchange elements and a body fluid, the surface area of those elements can be increased in several ways without significantly altering the overall cross-sectional volume of the catheter. Thus, for example, FIG. 11 illustrates a heat exchange region 210 on a catheter of the present invention wherein a plurality of undulating heat exchange elements 212 extend from a distal manifold 214 to a proximal manifold 216 provided on a shaft 218. Stated another way, the elements 212 extend in a non-linear path with at least one point of inflection. This configuration provides greater surface area for each heat exchange element 212 than the shallow convexity of elements 58, 102, and 166, previously described. Furthermore, the fact that each element 212 is located generally parallel to but spaced from the main shaft 218 permits them to compress inward and/or migrate around this circumference of the shaft when passing the catheter through narrow or tortuous body cavities.

Figure 12:
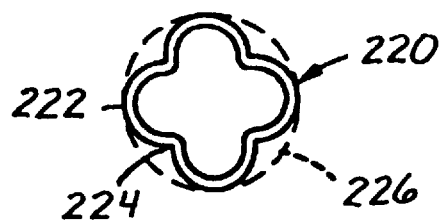
FIG. 12 is a sectional view through a hollow heat exchange element of the present invention having a non-circular configuration and greater surface area for heat transfer.

Another means for increasing the surface area of each heat exchange elements is to modify their cross-section from a purely circular cross-sectional geometry. Thus, FIG. 12 illustrates, in cross-section, a heat exchange element 220 having a plurality of alternating outwardly projecting regions 222 and grooves 224. The overall cross-sectional footprint, if you will, fits within an imaginary circle 226, but has a greater exterior surface area. Those of skill in the art will recognize that numerous cross-sectional configurations for the heat exchange elements satisfying the dual requirements of an increased surface area without increasing the overall cross-sectional footprint are possible.

An alternative construction for the heat exchange elements is shown in FIGS. 13 and 14. A catheter shaft 240 contains an inlet fluid flow lumen 242 and an outlet fluid flow lumen 244. A plurality of heat exchange elements 246 attach at only one end along the length of the shaft 240 so that they may float freely in surrounding body fluid. Each heat exchange element 246 comprises an outer tubule 248 surrounding an inner tubule 250. The distal end of the outer tubule 248 is closed and the distal end of the inner tubule 250 is open and terminates short of the distal end of the outer tubule. The inner tubules 250 define lumen therein that are in fluid communication with the inlet lumen 242. In addition, the outlet lumen 244 is in fluid communication with the annular space between the inner tubule 250 and outer tubule 248. In this manner, heat transfer fluid traveling through the inlet lumen 242 of the shaft of the catheter enters the inlet tubule lumen, as indicated by arrows 252, and flows between the inner and outer tubules and into the outlet lumen 244 of the shaft, as indicated by arrows 254. The heat exchange medium circulation path in this case includes so-called cul-de-sac heat exchange elements. The outer surface of the outlet tubule is surrounded by body fluid, for example blood, and as heat transfer fluid circulates through the tubules, heat may be transferred between the heat transfer fluid and the body fluid. It should be noted that the direction of fluid flow could be reversed, and the flow structure need not be precisely as illustrated. For example, the inlet and outlet lumen in the shaft need not be concentric, other configurations are possible.

A still further alternative construction for the heat exchange elements is shown in FIGS. 15–20. This embodiment includes a proximal manifold 300 and a plurality of heat exchange elements 302, wherein proximal portions of the individual heat exchange elements 302 are bundled or positioned within a shaft or sleeve 306. Distal portions of the heat exchange elements 302 protrude out of and freely extend beyond the distal end of the sleeve 306.

Figure 15:
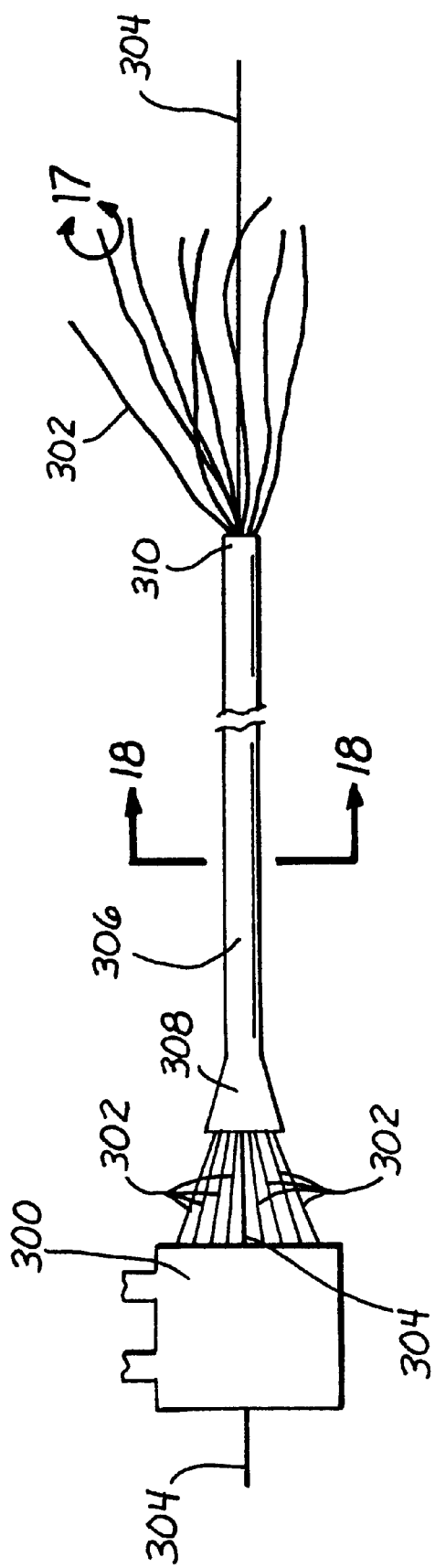
FIG. 15 is a side view of a heat exchange catheter of the invention having coaxial heat exchange elements.

With particular reference to FIG. 15, the catheter includes a guidewire tube 304 that extends through the proximal manifold 300 and beyond the distal ends of the heat exchange elements 302. The sleeve 306 may comprise a flexible tubular structure that substantially surrounds the multiple heat exchange elements 302 (that comprise flexible tubes) and the guidewire tube 304, along substantially the entire length of the catheter. The portions of the heat exchange elements that protrude beyond the distal end of the sleeve 304 define the heat exchange region of this particular, embodiment of the invention. Optionally, the tubular sleeve 306 may be flared at a proximal end 308 to facilitate convergence of the multiple heat exchange elements 302 into a single, low-profile tube.

The heat exchange elements 302 are unconstrained and float freely with the body fluid beyond a distal end 310 of the tubular sleeve 306. The embodiment illustrated shows eight heat exchange elements 302, although other numbers are possible. The guidewire tube 304 is generally stiffer than the heat exchange elements 302. A temporary attachment means (not shown) may initially be provided to couple the loose portions of the heat exchange elements 302 and the guidewire tube 304 or a temporary adhesive releasably attaching the heat exchange elements to the guidewire tube. Such attachment means may be in the form of an elastomeric band around all of the heat exchange elements 302 and the guidewire tube 304. Such a weak, temporary attachment may be overcome when the elements 302 are inflated during operation of the catheter, or may be severed by other suitable means.

Figure 17:
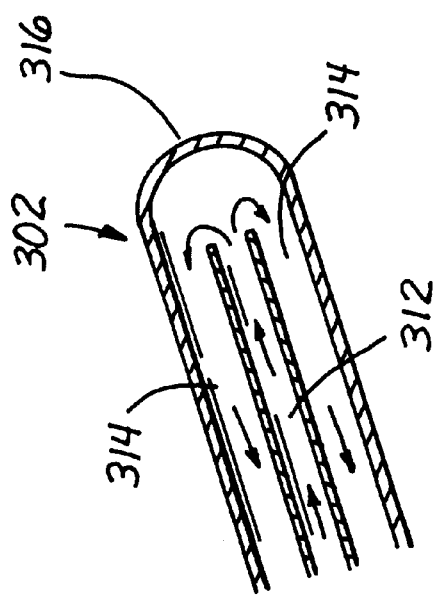
FIG. 17 is an enlarged cross sectional view of the distal tip of one of the coaxial heat exchange elements.
Figure 18:
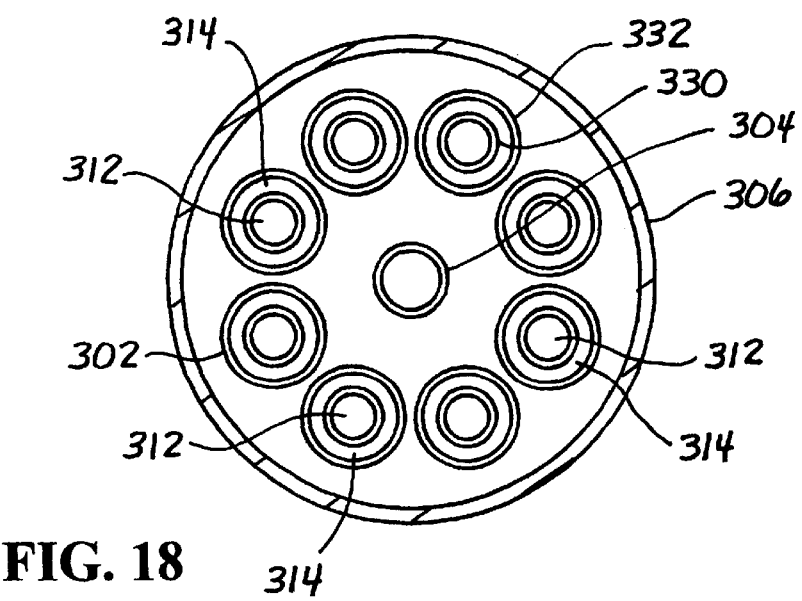
FIG. 18 is a cross sectional view of the proximal shaft portion of the heat exchange catheter taken along line 18—18 of FIG. 15.

As seen in the detailed view of FIG. 17 and cross-section of FIG. 18, the heat exchange elements 302 comprise coaxial tubes, each having an inner lumen 312 and an outer lumen 314. At the distal end 316 of each of the elements 302, the outer lumen 314 is closed, and the inner lumen terminates short of this distal end. The flow arrows show heat exchange medium passing distally through the inner lumen 312, and being re-directed at the distal end 316 to travel proximally through the outer lumen 314.

Figure 16:
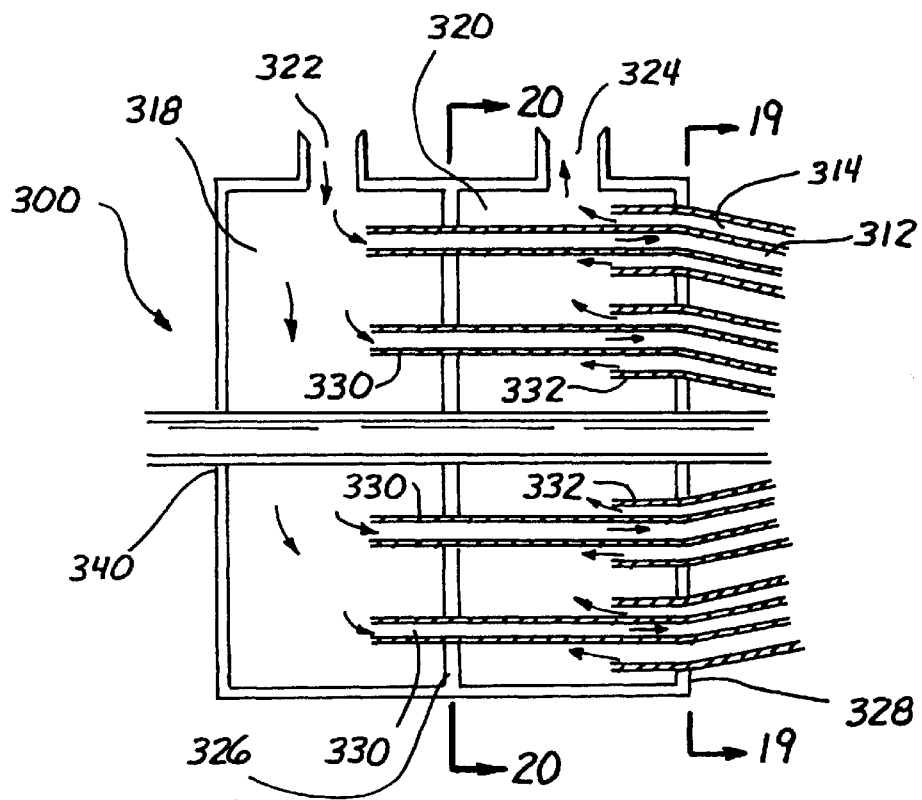
FIG. 16 is a cross-sectional view of the proximal manifold for the heat exchange catheter of FIG. 15.

As seen in FIG. 16, the proximal manifold 300 comprises a container generally divided into two equal chambers; an inlet chamber 318, and an outlet chamber 320. The inlet chamber 318 has a fluid inlet port 322, and the outlet chamber 320 has a fluid outlet port 324. The two chambers 318, 320 are separated by a divider plate 326. Each of the heat exchange elements 302 passes through a front plate 328 of the manifold 300.

As seen in FIGS. 16 and 17, the inner lumen 312 are defined within input tubes 330 terminating in the inlet chamber 318. Likewise, the outer lumen 314 are defined within output tubes 332 terminating in the outlet chamber 320. The input and output tubes 330, 332 pass through holes 334 formed in the front plate 328, as seen in FIG. 19. Each of the holes 334 fluidly seals around the tubes 330, 332. A central hole 335 for passage of the guidewire tube 304 is also provided in the front plate 328. The guidewire tube 304 extends in a sealed manner through the central hole 335. With reference to FIG. 20, the divider plate 326 includes a central hole 338 fluidly sealed around the guidewire tube 304. The guidewire tube 304 continues through a single hole 340 provided in the back plate of the manifold 300. Each input tube 330 passes through a hole 336 in the divider plate 326, and is fluidly sealed with respect thereto.

In use, the catheter is inserted into a blood vessel and heat exchange fluid is introduced through the inlet port 322 and into the inflow chamber 318. The heat exchange fluid then passes into the open proximal ends of each of the inlet tubes 330, and into the inner lumen 312 of each of the heat exchange elements 302. The fluid passes along the length of each of the heat exchange elements 302 until it is re-directed at the distal end 316 into the outer lumen 314. The fluid then travels proximally through the outer lumen 314, as seen FIG. 17, until it reaches the open proximal ends of each of the outlet tubes 332. If the heat exchange elements 302 are initially in a collapsed configuration, the flow of heat exchange fluid inflates them and may cause severance of an attachment means and subsequent separation of each of the elements. The fluid ultimately passes into the outlet chamber 320 and exits the manifold 300 through the outlet port 324. In this manner, heat exchange fluid may be circulated through the heat exchange catheter. As the heat exchange fluid returns proximally through the outer lumen 314, it exchanges heat with blood flowing past the surface of the elements through the outer wall of the heat exchange elements 302.

While the example given shows fluid circulating distally through the inner lumen 312, and proximally through the outer lumen 314, those of skill in the art will appreciate that the direction of flow may sometimes be reversed by merely introducing heat exchange fluid into the inlet chamber, while removing it from the outlet chamber. It is generally desirable to have counter-current heat exchange, that is, that the blood flow is in the opposite direction to the flow of the heat exchange fluid in the outer lumen 314. If the heat exchange elements 302 are in the bloodstream such that the distal ends of the elements are downstream, and blood is flowing from proximal to distal along the surface of the catheter, the inlet flow of heat exchange fluid is desirably through the inner lumen 312 and the outlet flow is desirably through the outer lumen 314. This flow arrangement is preferred for the catheter with free-floating heat exchange elements on the distal end, because even if the blood flows distal to proximal, the elements tend to prolapse and float backward toward the proximal end of the catheter. In such a configuration, counter flow is achieved if the heat exchange fluid is flowing back out of the catheter through the outer lumen 314.

With reference now to an alternative embodiment shown in FIG. 26, a heat exchange catheter 350 of the present invention includes a plurality of heat exchange elements that are formed of a loop of single lumen tubing that extends the entire length of the catheter. The inlet end of each of the single lumen tubes is open to an inlet reservoir of a manifold, and the outlet end is open to the outlet reservoir. Heat exchange fluid circulates along the entire length of each of the heat exchange elements.

Figure 21:
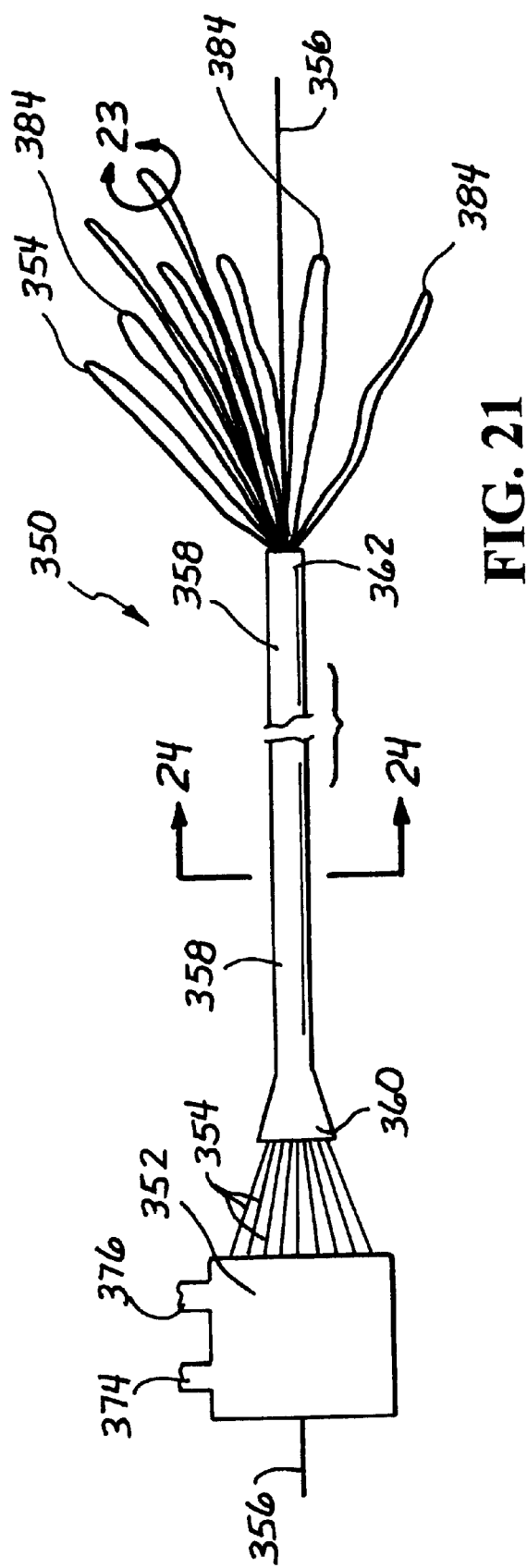
FIG. 21 is a side view of a heat exchange catheter of the invention having single loop heat exchange elements.

Referring particularly to FIG. 21, a single loop heat exchange catheter 350 comprises a proximal manifold 352, a plurality of coaxial heat exchange elements 354, a guidewire tube 356, and a proximal tubular sleeve 358 that surrounds the heat exchange elements in the proximal region of catheter. The catheter 350 illustrated shows eight such heat exchange elements 354, each comprising loops of long single lumen tubes. Of course, those of skill in the art will understand that the number of heat exchange elements may be varied. The proximal end 360 of the tubular sleeve 358 may be flared to facilitate a convergence of a the multiple heat exchange elements 354 into a single, lower profile tube.

At the distal end 362 of the sleeve, the heat exchange elements 354 are unconstrained and may float freely. The guide wire tube 356 is generally stiffer than the heat exchange elements 354, and a loose attachment (not shown) may temporarily be formed therebetween. For example, an attachment means such as elastomeric band around all of the heat exchange elements 354 and the guidewire tube 356 may be used. Alternatively, any weak, temporary attachment means that can be overcome when the elements 354 are inflated can be substituted.

Figure 22:
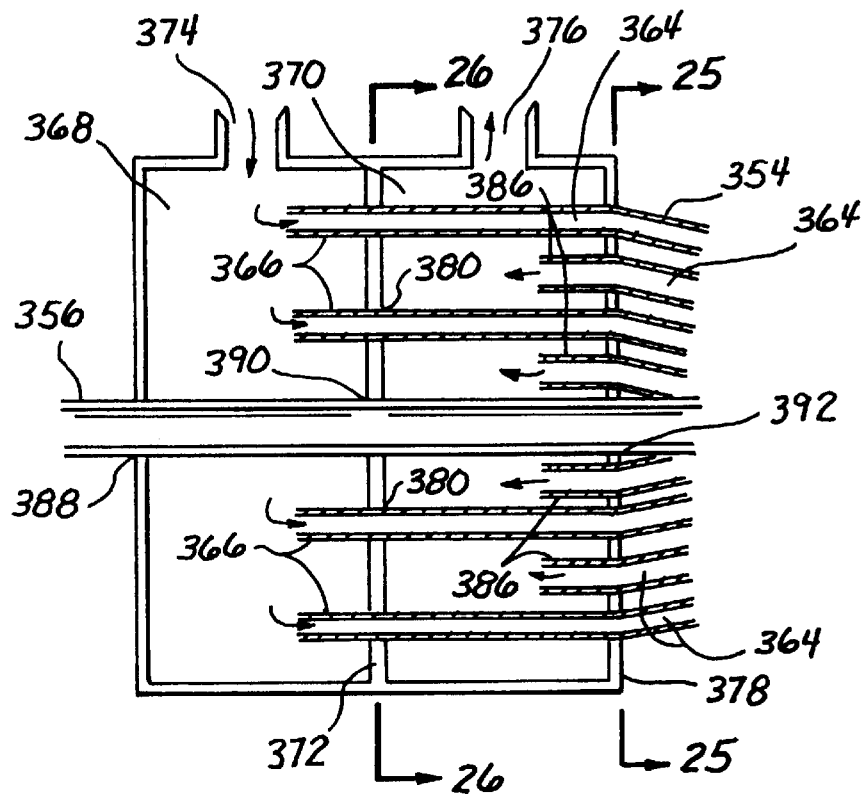
FIG. 22 is a cross-sectional view of the proximal manifold for the heat exchange catheter of FIG. 21.
Figure 24:
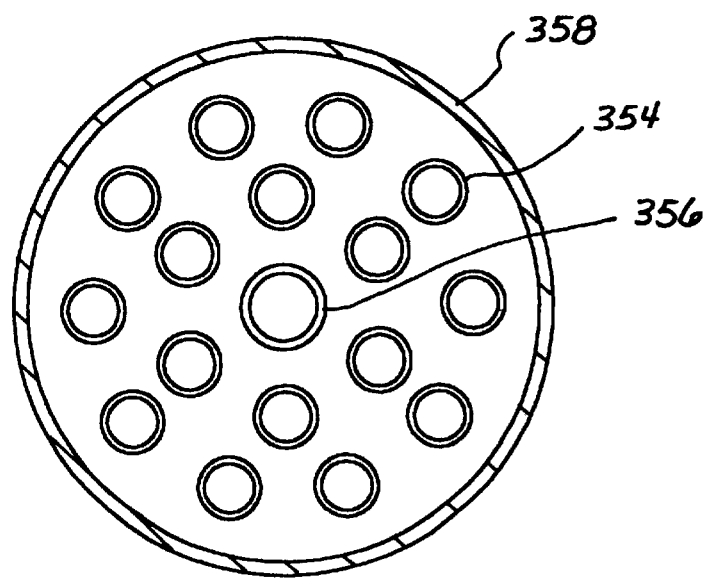
FIG. 24 is a cross-sectional view of the proximal shaft portion of the heat exchange catheter taken along line 24—24 of FIG. 21.

As seen in FIG. 22, the proximal manifold 352 defines within two reservoirs; an inflow reservoir 368 an outflow reservoir 370. A divider plate 372 separates the two reservoirs 368, 370. An inflow port 374 communicates with the inflow reservoir 368, while on outflow port 376 communicates with the outflow reservoir 370. A front plate 378 forms the front surface of the manifold 352, as seen in plan view in FIG. 25.

Figure 23:
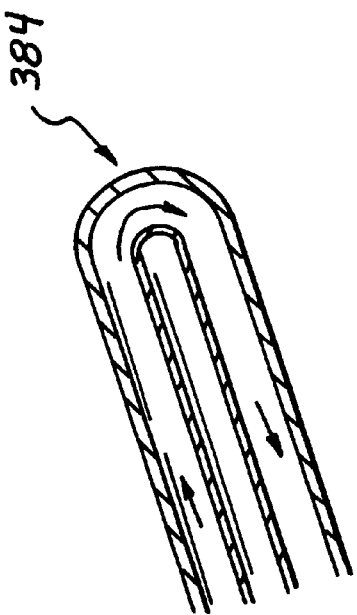
FIG. 23 is an enlarged cross-sectional view of the distal tip of a single loop heat exchange element.

The heat exchange elements 354 comprise long, thin-walled tubes, each defining a single lumen 364 therein. Each tube has an open end 366 positioned in the inflow reservoir 368 and extends distally through sealed apertures 380 in the divider plate 372 (FIG. 26). The tubes pass through the outflow reservoir 370 and through sealed apertures 382 in the front plate 378 (FIG. 25). The tubes continue distally, converging in the flared portion 360 of the tubular sleeve 358, and emerging from a distal end 362. Each of the heat exchange elements 354 extends for some distance to a distal bend 384, seen in FIG. 23. The distal flow of heat exchange fluid is thus re-directed proximally at the distal bend 384. The return tube again passes through one of the apertures 382 in the front plate 378, and terminates in the outflow reservoir 370.

A guidewire tube 356 passes entirely through the manifold 352, extending through a proximal guidewire hole 388, a central aperture 390 in the divider plate 372, and a central aperture 392 in the front plate 378. The guidewire tube 356 is sealed from both reservoirs 368,370 in the manifold 352.

In use, heat transfer fluid (represented by the arrows in the various FIGS) is introduced into the inflow reservoir 368 through the inflow port 374. The pressurized fluid passes into the open ends of each of the heat exchange element tubes 354, flows the entire length of the tube and is redirected at the bend 384, and then flows proximally, emptying into the outflow reservoir 370. The fluid is then exhausted through the outlet port 376. As previously stated, those of skill in the art will understand that the direction of flow may be easily reversed without altering the basic principles of the invention. In this embodiment, however, the heat exchange fluid will be flowing in both directions in a tube in contact with the blood flow, and therefore both co- and counter-current flow will exist. Thus, the direction of flow through the tubes becomes less significant than in the coaxial arrangement described above.

The heat exchange elements of the present invention may be formed from a variety of materials, the main consideration being biocompatibility. The elements are fluid impermeable, preferably some form of polymer, and flexible. One particularly useful material is polyethylene terephthalate (PET) which can be extruded and blown to form thin-walled hollow filaments.

While a particular embodiment of the invention has been described above, for purposes of or illustration, it will be evident to those skilled in the art that numerous variations of the details may be made without departing from the invention as defined in the appended claims. By way of example and not limitation, where heat is exchanged between two flowing fluids, as between the flowing heat exchange fluid in this catheter and flowing blood, it has been found that the heat exchange if more efficient if there is counter-current flow between the fluids, that is that the fluids are flowing in opposite directions. In the example given here, the blood may be flowing past the heat exchange filaments from proximal to distal or from distal to proximal depending on the means of inserting the catheter. For example, if the catheter is inserted into the inferior vena cava through a jugular vein incision, the blood would flow over the heat exchange region from the distal end toward the proximal end of the catheter (i.e., retrograde flow), whereas if the catheter is inserted into the inferior vena cava from a femoral vein incision, the blood would flow past the heat exchange region from proximal toward distal (i.e., antegrade flow). In order to achieve counter-current flow between the blood and the heat exchange fluid, the inlet and outlet lumen of the shaft may be reversed without departing from the invention as described. Similarly other variations of the embodiments described are anticipated within the scope of the invention as claimed.

What is claimed is:

1. A heat exchange catheter comprising:
   an elongate catheter shaft having an inflow lumen and an outflow lumen extending at least partially therethrough;

at least one undulating tubular heat exchange element having a first end that is connected to the inflow lumen of the catheter shaft and a second end that is connected to the outflow lumen of the catheter shaft, such that heat exchange fluid may be circulated through the inflow lumen, then catheter shaft, such that heat exchange fluid may be circulated through the inflow lumen, then through the undulating tubular heat exchange element and then through the outflow lumen; and an insulator disposed about the catheter shaft proximal to the heat exchange element.

2. A catheter device according to claim 1 having a plurality of said undulating tubular heat exchange elements.

3. A catheter device according to claim 2 further comprising a first manifold for channeling heat exchange fluid from the inflow lumen of the catheter shaft into the first ends of the plurality of undulating tubular heat exchange elements and a second manifold for channeling heat exchange fluid from the second ends of the undulating tubular heat exchange elements and into the outflow lumen of the catheter shaft.

4. A catheter device according to claim 1 wherein the insulator extends over approximately 85–90% of the length of the catheter shaft.

5. A catheter device according to claim 1 wherein the insulator comprises an inflatable insulating balloon.

6. A catheter device according to claim 1 wherein the catheter shaft is within the insulating balloon and a plurality of stand-offs are interposed between the insulating balloon and the catheter shaft.

7. A catheter device according to claim 1 wherein the insulator comprises a plurality of insulating balloons surrounding the catheter shaft and a sleeve that substantially encompasses the insulating balloons.

8. A catheter device according to claim 1, wherein the catheter shaft has a length and the undulating tubular heat exchange element is mounted on a portion of the catheter shaft, said portion consisting of less than one half the length of the catheter shaft.

9. A catheter device according to claim 1 wherein the at least one undulating tubular heat exchange element is disposed generally parallel to the catheter shaft.

10. A catheter device according to claim 9 wherein the at least one undulating heat exchange element is spaced apart from the catheter shaft such that, when the catheter device is inserted into a blood vessel, blood may flow between the undulating heat exchange element and the catheter shaft.

\* \* \* \* \*